United States Patent [19]
Bredehorst et al.

[11] Patent Number: 5,433,955
[45] Date of Patent: Jul. 18, 1995

[54] SITE SPECIFIC IN VIVO ACTIVATION OF THERAPEUTIC DRUGS

[75] Inventors: Reinhard Bredehorst, Washington, D.C.; Chong-Ho Kim; Richard McCabe, both of Rockville, Md.; Nicholas Pomato, Frederick, Md.; Carl-Wilhelm Vogel, Washington, D.C.

[73] Assignee: Akzo N.V., Arnhem, Netherlands

[21] Appl. No.: 134,520

[22] Filed: Oct. 8, 1993

Related U.S. Application Data

[63] Continuation of Ser. No. 720,837, filed as PCT/US90/00503, Jan. 23, 1994, abandoned, which is a continuation-in-part of Ser. No. 300,999, Jan. 23, 1989, abandoned.

[51] Int. Cl.$^6$ .................. A61K 37/58; A61K 31/70; C12N 11/06; C07H 15/252
[52] U.S. Cl. .................. 424/94.3; 424/94.61; 530/388.15; 514/34; 514/55; 536/20; 536/6.4; 435/177
[58] Field of Search .................. 435/7.21, 7.23, 7.24, 435/206, 174, 177, 178; 424/85.91, 94.1, 94.3, 94.61; 530/388.1, 388.15, 391.1–391.9; 514/34, 55; 536/20, 6.4

[56] References Cited

U.S. PATENT DOCUMENTS

| | | | |
|---|---|---|---|
| 4,067,774 | 1/1978 | Rubenstein | 435/188 |
| 4,804,750 | 2/1989 | Nishimura et al. | 536/20 |
| 4,975,278 | 12/1990 | Senter et al. | 424/94.3 |

OTHER PUBLICATIONS

Bagshawe, Br. J. Cancer (1987), vol. 56 (5), pp. 531–532.
Bagshawe, Br. J. Cancer (1988), vol. 58, pp. 700–703.
Springer et al, Abstract 43 from Thrird International Conference on Monoclonal, Antibody/Immunoconjugates for Cancer, Feb. 4–6, 1988, San Diego, Calif.

*Primary Examiner*—Jacqueline Stone
*Attorney, Agent, or Firm*—William M. Blackstone; Mary E. Gormley

[57] ABSTRACT

A method for site-specific in-vivo activation of a prodrug in an animal using an activator-targeting moiety conjugate to localize an activator at a predetermined site of use and a prodrug compound that is converted to an active drug in the presence of the activator. In the preferred embodiment, the targeting moiety, the activator, and the prodrug demonstrate little or no immunogenicity in the animal being treated. The targeting moiety is relatively specific for binding to the target tissue than to non-target tissue. The activator is not found or present in only small amounts in circulation or in non-target tissue, does not have a substrate for its activity in circulation or in non-target tissue, can be linked to the targeting moiety, and is capable of converting the prodrug to an active drug. The prodrug is selected for its ability to exert a cytotoxic activity on the target tissue after conversion by the activator.

17 Claims, 14 Drawing Sheets

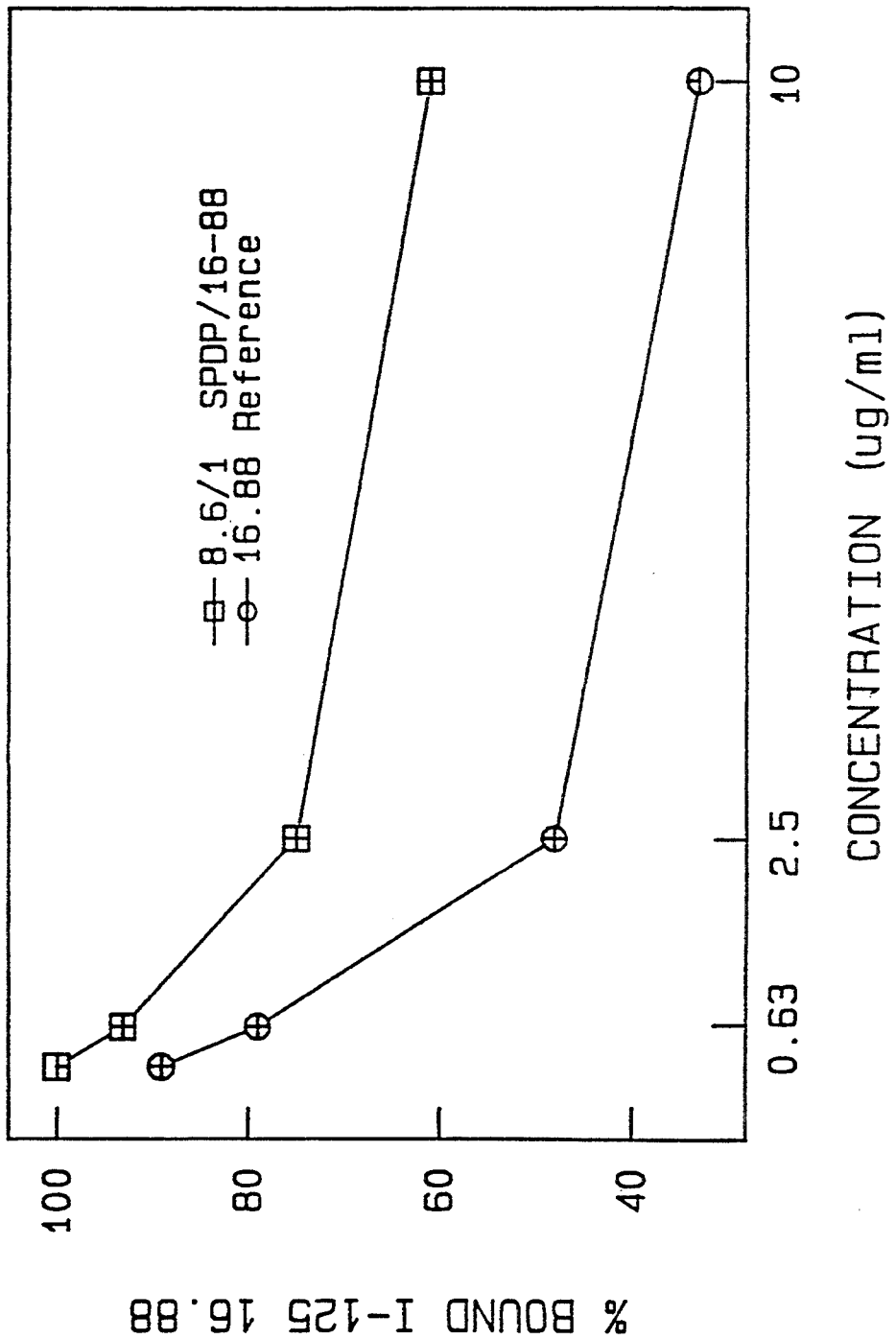

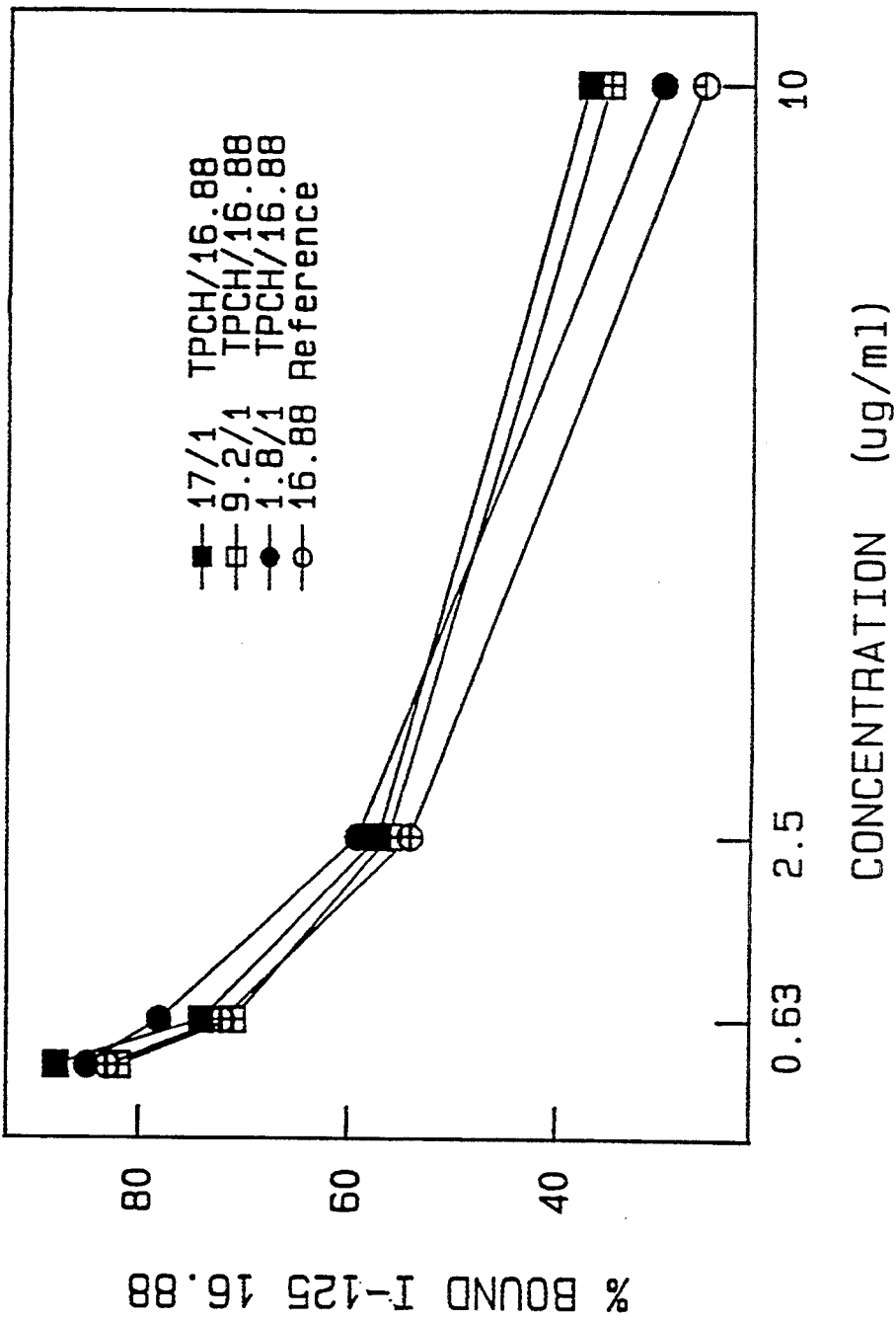

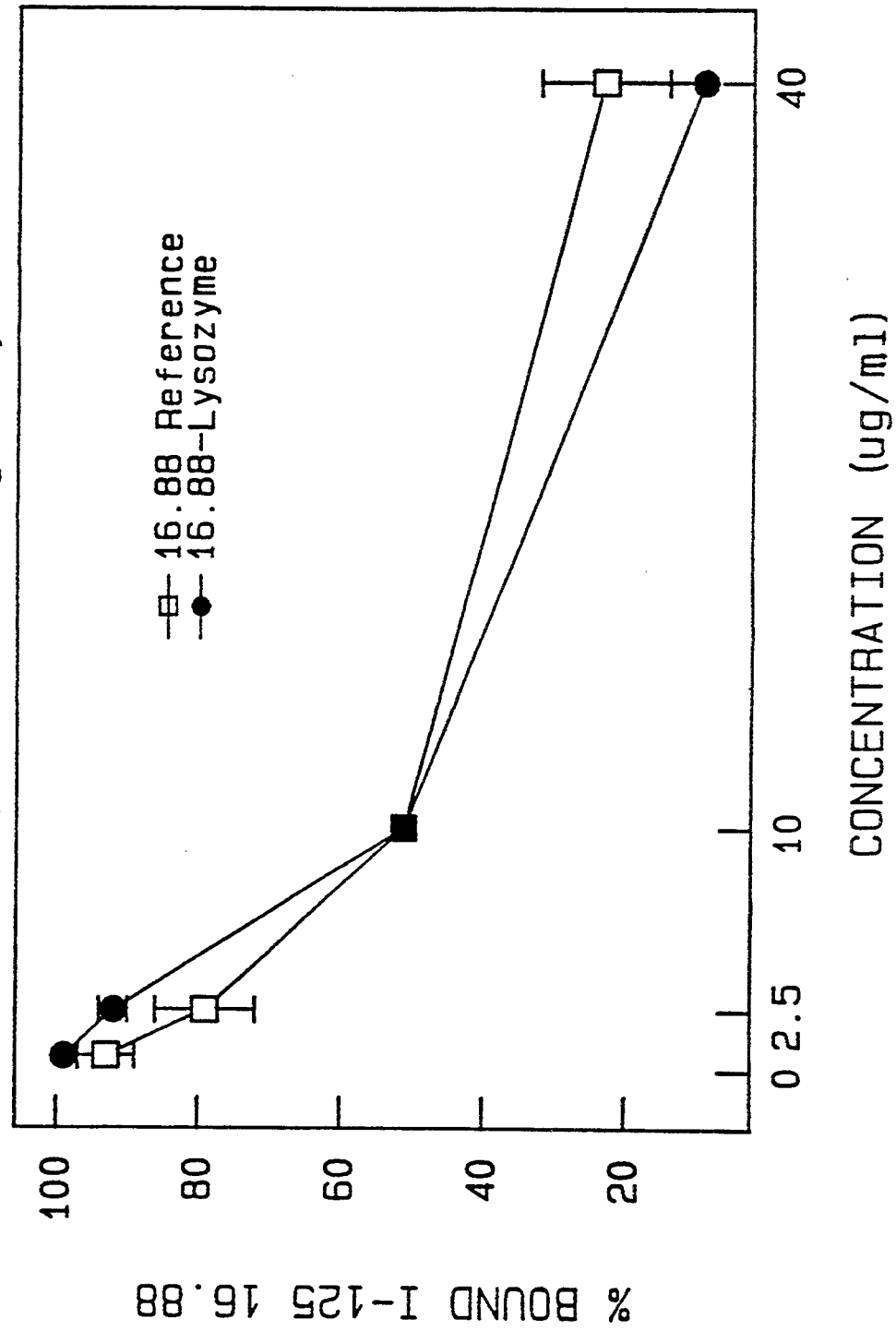

a; n=0
b; n=1
c; n=2
d; n=3
e; n=4
f; n=5
g; n=6 tion of application Ser. No. 07/720,837, filed as PCT/US90/00503, Jan. 23, 1990, now abandoned, which is a continuation-in-part of the U.S. application Ser. No. 07/300,999, filed Jan. 23, 1989, now abandoned.

SITE SPECIFIC IN VIVO ACTIVATION OF THERAPEUTIC DRUGS

This is a continuation of application Ser. No. 07/720,837, filed as PCT/US90/00503, Jan. 23, 1990, now abandoned, which is a continuation-in-part of the U.S. application Ser. No. 07/300,999, filed Jan. 23, 1989, now abandoned.

DESCRIPTION OF THE INVENTION

This invention relates to therapeutic systems site specific activation of therapeutic agents, including the chemistry of therapeutic agents, delivery of therapeutic agents to sites of disease, control of specific non-target organ toxicity and control of general side effects related to the use of the therapeutic agents.

BACKGROUND OF THE INVENTION

Drugs are generally not selective for their target organs or cells and, as a result, they exert toxic side effects. The concept of coupling a therapeutic agent to a carrier molecule (e.g. antibody) with specificity for a defined target cell population is, therefore, an attractive one to achieve site-specific drug delivery. In recent years, for example, a variety of monoclonal antibodies that recognize tumor associated cell-surface antigens have been used as carriers of many of the clinically used anticancer agents, as reviewed in Vogel, C. -W., 1987. Specific and potent cytotoxic activities of such immunoconjugates have been described by investigators in a variety of in vitro systems. Less impressive and even disappointing results were obtained when such immunoconjugates were studied for their immunotherapeutic activity in tumor-bearing animals as well as in cancer patients. These data demonstrate that the concept of immunoconjugates poses a number of difficulties yet to be overcome as it has not been possible to deliver sufficient quantities of drugs coupled to monoclonal antibodies (for review see Vogel., C. -W. 1987).

Early on it was recognized that enzymes may be superior to drugs. Ribosomal inactivating proteins (RIP's) are enzymes and their cytotoxic effect is potentisted by this enzymatic activity. However, like drugs RIP's must be internalized, liberated from the antibody carrier and reach the appropriate intracellular compartment to exert their activity. Moreover, RIP's require antigen expression by every target cell to be effective and they have an inherent cytotoxicity that limits the amount that can be given.

Another enzymatic approach uses a surface active enzyme coupled to an antibody. This antibody-enzyme conjugate would not require internalization and could exert cytotoxic activity on cells in the area. One example of a surface active enzyme that has been used as an antibody conjugate is phospholipase-C, which attacks the phospholipids of all cell membranes directly without requiring internalization. However, the ability of phospholipase to attack the phospholipids in all cells expresses an inherent cytotoxicity, which limits its usefulness (Flickinger and Trost, 1976). Another surface active enzyme used as an antibody conjugate is cobra venom factor (CVF), a complement activating enzyme, which, in addition to not needing to be internalized by the cells, is not inherently cytotoxic (Vogel, C. -W., 1987). However, like all foreign proteins, CVF is highly immunogenic and its use for treating tumor cells is, therefore, limited.

A further approach used antibody-alkaline phosphatase conjugates for dephosphorylation of an etoposide derivative. The problems with this approach are competition with circulating endogenous substrates limiting the enzymatic activity at the target and a high level of enzyme activity in circulation and in non-target tissues, resulting in an increase in unwanted cytotoxic activity (Senter et al, 1988).

A different enzymatic concept used carboxypeptidase-$G_2$, which cleaves an essential growth factor, folate (Searle et al, 1986). However, a sufficient decrease in folate level requires a higher level of enzyme conjugate in the target tissue than can be achieved using an antibody-enzyme conjugate in-vivo.

In addition to the particular disadvantages as described above, all enzymatic approaches share the problem of immunogenicity. The development of antibodies against the enzymes results in inactivation of the activity by blockage and steric hindrance and rapid clearance of the anti-bodyenzyme from the circulation. For this reason the system suggested by Bagshawe, K. D. (1987) using an enzyme-antibody conjugate for drug activation would, at best, provide useful results in only a single administration, and the immune response may prevent efficacy even then. Bagshowe's concept uses non-mammalian enzymes that do not have human analogues to avoid activation by enzymes other than on the conjugate. However, these enzymes would be highly immunogenic, particularly when conjugated.

SUMMARY OF THE INVENTION

We have conceived of a novel approach to drug delivery using a targeted enzyme that circumvents the limitations mentioned above. We propose a two-step procedure. First, an essentially non-immunogenic targeting moiety-activator conjugate comprising an activator, typically an enzyme, coupled with a targeting moiety. In the preferred embodiment the targeting moiety is an antibody which binds to a tumor associated antigen located on the cell surface or in an extracellular area (e.g. necrotic area) of the tumor. The antibody-activator conjugate is specifically retained at the tumor. If necessary, non-bound conjugate is allowed to clear from the circulatory system sufficiently to avoid toxic side effects. If necessary, this process can be accelerated in-vivo by complex formation or ex-vivo by adsorption to a specific matrix. Second, a relatively nontoxic drug derivative (prodrug) that can not be taken up by cells is administered. At the tumor site the drug derivative is "activated" by the antibody-bound enzyme, converting the prodrug to a drug molecule, which is able to enter antigen-positive as well as antigen-negative tumor cells at the tumor site and exert its activity. In addition, our approach allows repeated administration of the non-immunogenic prodrug, thereby powerfully amplifying the efficacy of this therapeutic approach. Furthermore, this approach is not limited to anti-tumor therapy but is applicable in any system when site-specific delivery of a therapeutic agent is needed. Examples of other diseases with which this method of site specific activation can be used include infectious diseases, autoimmune diseases and other inflammatory diseases. The targeted site of activation may be, therefore, a particular tissue, or a particular type of cell, including infectious organisms.

An advantage of the invention is that the conjugates need not be internalized into the target cell. Thus, repeated and long-term conversion of prodrug in the patient, including repeated injections of the antibody-activator conjugates, can be maintained.

Certain requirements must be met for our invention. First, the targeting moiety (e.g., antibody) and the activator (e.g., enzyme) bound to the targeting moiety have to be of an origin compatible with the species being treated to prevent immunological inactivation of the conjugates. In the case of treating humans, they should be of human origin or human-like, either by being genetically conserved or by being from a genetically similar species, and thus be essentially non-immunogenic to prevent the development of antibodies against these molecules. Also, the prodrug must be essentially non-immunogenic. The development of antibodies against foreign proteins in immunoconjugates (e.g. murine antibodies) has been shown to occur. Human anti-mouse antibody formation in cancer patients has been reported after single injections of murine monoclonal antibodies (McCallister et al, 1988), thereby limiting the applicability of these agents to a single course of therapy. Many individuals even have pre-existing levels of antibody to murine immunoglobulin prior to receiving their first dose of murine antibody (Schroff, R. W. et al, 1985). Furthermore, after two or more injections, antibody responses to even poorly immunogenic antibody Fab fragments can be detected in 50% of the patients (Reynolds, J. C. et al, 1986). Thus, by essentially non-immunogenic we mean that the activator-targeting moiety conjugate and the prodrug can be administered to a patient repeatedly without inducing an immune response in the patient that inhibits localization of the conjugates, activation of the prodrug, or activity of the activated drug to a degree that prevents therapeutic efficacy.

A second requirement is that the antibody-bound enzyme shall have essentially no naturally occurring substrate in the circulation or on the surface of non-target cells. The presence of naturally occurring substrate in the host is disadvantageous because it will compete with activation of the prodrug and result in less prodrug being activated. The absence of naturally occurring substrates is also important to avoid detrimental side effects from the enzymatic activity in the host prior to localization of the antibody-activator conjugate. Accordingly, enzymes such as phospholipase-C and phosphatases are not suitable for our invention, as they have natural substrates in humans. We define "essentially no naturally occurring substrate" as the absence of substrate in amounts that, in contact with activator on the administration of conjugate, would prevent therapeutically effective conversion of prodrug to drug at the sites of tumors. Also, the substrate cannot be present in amounts that would cause detrimental side effects from enzymatic activity on naturally present substrate.

A third important requirement for our invention is that the enzymatic activity of the conjugate must essentially not be present or present in only very low quantities in the circulation or on the cell surface of non-target organs to avoid non-targeted prodrug activation, which would result in activation at other than the tumor site. For example, alkaline phosphatase, an enzyme present in human serum at rather high levels, is shown to dephosphorylate low molecular weight compounds within a few minutes in human serum (Hamm et al, 1988). Enzymatic activity present in low amounts may be further decreased to meet the requirement of this invention by clearing the circulation of the antibody. This can be done in-vivo by formation of immune complexes or ex-vivo by adsorption to a specific matrix. Enzymatic activity of the conjugate being essentially not present is defined as prodrug not being activated at locations other than at tumor sites to a degree that inhibits the therapeutic effect of the drug or causes unwanted cytotoxicity in non-tumor tissue, or both.

DESCRIPTION OF THE PREFERRED EMBODIMENTS

The examples described below use a human monoclonal IgM antibody and human lysozyme as the activator and a doxorubicin derivative as the effector component (prodrug). This system illustrates the advantages of our invention, which are:

(a) all components, the targeting moiety, the activator and the prodrug, are essentially non-immunogenic, allowing repeated targeting as well as repeated administration of the prodrug;

(b) the antibody effector complex is non-toxic thus allowing large quantities of the complex to be administered. The prodrug exerts its full cytotoxic activity only after activation;

(c) Internalization of the conjugate is not required, thus repeated conversion of the prodrug to drug can be employed on successive administrations;

(d) antigen expression in target tissue is not required by all cells because drug molecules after conversion are able to enter antigen positive as well as antigen negative cells;

(e) lysozyme does not have a naturally occurring substrate for its activity in humans, thereby avoiding competition for lysozyme activity and the concomitant detrimental effects (The natural substrate of lysozyme are polymers from bacterial cell walls consisting of alternating N-acetylmuramic acid and N-acetylglucosamine residues.); and (f) lysozyme occurs in the circulation only in very low quantities, derived from lysozyme containing leukocytes, and is not expressed on cell surfaces (Briggs et al, 1966).

The method of our invention, however, is applicable to a variety of antibodies and activator systems that meet the basic requirements and the concept is not limited to lysozyme activator systems. Indeed, one of the advantages of our approach is that it is much more permissive regarding the characteristics of the antibody than a system requiring antibody internalization by target cells. Moreover, the activator need not be an enzyme, but any compound that functions to convert a prodrug to an active moiety, such as, for example, a catalytic antibody (Napper et al, 1987).

Choice of Targeting Moiety

According to the present invention, antibodies directed against any antigen may be used as the targeting moiety. In addition to antibodies, other molecules that have affinity for the specific cells, types of tissue or infectious agents targeted may be used as targeting moieties. For example, cytokines have particular specificity for certain types of cells and can be used as targeting moieties. Although other types of molecules than antibodies can be used as the targeting moiety, such as antigens, antibody fragments, lectin, hormone or ligand, for simplicity in the following discussion the term antibody will be used with the intention that other types of targeting moieties can be used in their place.

Conventional polyclonal antibodies may be applied as carrier molecules within the concept of the invention. However, monoclonal antibodies offer multiple advantages. Each monoclonal antibody is specific for one antigenic determinant. Thus, with monoclonal antibodies the extent of non-specific binding to normal tissues and subsequent toxicity to normal non-target tissues is reduced. In addition, since unlimited amounts of each monoclonal antibody can be produced, all individual preparations of antibody can be controlled to ensure that antigen specificity remains constant over the life of the antibody product. Different monoclonal antibodies specific for different epitopes with the same tissue specificities may be combined. Thus, when using a monoclonal antibody or a mixture of monoclonal antibodies the efficacy and control of the delivery system is improved without sacrificing any contributions to the efficacy of the system that may be obtained with conventional polyclonal reagents.

A preferred approach is to se monoclona or polyclonal antibodies of the same species of origin as the animal receiving therapy. For the most part, with the exception of veterinary applications, the use of human, humanized or chimeric antibodies primarily human in their construction, is most desirable. Many human monoclonal antibodies have been described. Also, approaches to humanizing antibodies developed from lymphoid cells of non-human species and methods using variable region genes from non-human antibodies genetically coupled to human antibody constant region genes have been described. The advantages of the homologous and genetically engineered antibodies are several. Unlike heterologous, e.g., murine or rat antibodies, the immune response to the homologous antibody is minimal. At most, a weak response to idiotypic determinants of the human antibody occurs and then only after multiple cycles of administration. In our clinical studies with human monoclonal antibody 16-88 we have not detected any induction of an immune response to any region of the antibody, idiotypic, allotypic or framework, even after repeated doses of up to 200 mg/week (Steis et al, 1990). This advantage allows use of intact whole immunoglobulin rather than more rapidly metabolized antibody fragments, allows high doses of intact whole immunoglobulin to be administered and allows the use of multiple cycles of antibody administration. Antibodies raised in homologous species have additional advantages, as they recognize subtle antigenic differences not recognized by heterologous antibodies or even genetically engineered human antibodies.

Antibody may be directed against any target, e.g., tumor, tissue, bacterial, fungal, viral, parasitic, mycoplasmal, histocompatibility or differentiation antigens or receptors and etc. Antibody may be from any class, IgG, IgA, IgE or IgM, and a combination of antibodies reactive to different antigenic determinants may be used. For simplicity the target will be referred to as target tissue in the following, which is any of these materials for which the targeting moiety has affinity.

In applications of the invention in which cytotoxic agents are activated in the environment of rumor cells, there is no requirement that the target antigen or antibody be internalized by the tumor cells for the cytotoxic agent to enter the cell, as is the case when antibody is chemically bound to the cytotoxic agent.

Choice of Activator

The activator activity should not normally be present in the circulation or accessible non-target tissues, or should be present at very low levels such that unwanted activation of the drug in the circulation and non-target tissues occurs to only a very limited extent, which does not result in detrimental side effects. Furthermore, substrates for the activator or inhibitors of the activator should not be present in circulation or in the target tissues to an extent that compromises the therapeutic benefit of the invention. Superior benefit is obtained if the conjugate is selected to be non-immunogenic by choosing an enzyme from the same species of origin as the animal receiving therapy or a nearly identical enzyme. Many enzymes are highly conserved through evolution such that the molecules isolated from lower species are nearly identical to the human enzyme.

The activator attached to the antibody may be an enzyme from any class; hydrolase, oxido-reductase, transferase, isomerase, lyase, or ligase, or an antibody with similar catalytic activities (ref. Napper et al, 1987).

The endoglycosidase lysozyme meets the above requirements for activator activity. In addition, its low molecular weight, single chain construction and well studied chemical and structural properties (Imoto et al, 1972) enable chemical linkage of the enzyme to an antibody. Lysozyme is a 129-130 amino acid basic endoglycosidase which is highly conserved. Lysozyme from species as diverse as chicken, quail and man are nearly identical with regard to the number of amino acid residues, number of primary amines and the amino acid residues involved in this catalytic mechanism. Lysozyme is stable from pH 2 to pH 11 at temperatures up to 77° C. Furthermore, lysozyme is unusually resistant to low concentrations of most denaturants. Full reduction of the disulfide bonds eliminates lysozyme enzymic activity. In man lysozyme is found in milk, tears, saliva, placenta, spleen, leukocytes and monocytes. Lysozyme in blood is derived from leukocytes and monocytes. Normal blood levels are about 1% of that of tears (Osserman and Lawlor, 1966). Lysozyme attacks the $\beta$-(1→4) linkage between N-acetyl-glucosamine (GlcNAc) and N-acetylmuramic acid in the cell walls of some bacteria and attacks chitin, linear $\beta$-(1→4) linked polymers of N-acetylglucosamine. Preferred substrates are polymers equal or larger than $(GlcNAc)_6$.

Linkage of Activator to Antibody

According to the method of the present invention the activator enzyme or catalytic antibody is linked to the targeting antibody in a manner that retains the ability of the complex to bind antigen and to activate the prodrug component. This is achieved by using homo or hetero bifunctional crosslinking agents or direct protein modifying reagents to introduce highly reactive groups into both the activator component and the targeting moiety. Derivatized with these reactive groups, activator and targeting components will be coupled through covalent linkage when mixed together.

Linkers may be introduced into proteins or peptides by reacting with amino, carboxyl, or sulfhydryl groups (Wawrzynczak and Thorpe, 1987) and into glycoprotein and carbohydrates after oxidation of the sugar to generate aldehydes (Sela and Hurwitz, 1987). The aldehydes may be reacted with amino groups on the linker (e.g., hydrazide) to form a Schiff's base (e.g., hydrazone).

Sulfhydryl groups can be generated from the cysteine residues of many biological molecules, including antibodies and enzymes. These residues can be derivatized with reactive groups without altering the biological function of the molecules. Among antibody molecules, all classes contain intrachain and interchain disulfide linkages, which stabilize the tertiary and quarternary structure of the molecule. In the case of the IgM class of antibodies, the heavy chain structure contains several disulfide bonds that may be derivatized following mild reduction without loss of antibody function. The free sulfhydryl groups then react with haloalkyl groups, p-mercuribenzoate groups and groups capable of Michael-type addition reactions including, for example, malemides and groups of the type described in Mitra and Lawton (1979).

The most frequently used methods of attachment to proteins are based on the attack of the nucleophilic epsilon amino groups of lysine. The amino group may react with carbonyl functions introduced by highly reactive succinimide esters, anhydrides or cyclic thio esters, or by activating carbonyl functions with carbodiimides to form carboxamide bonds. Alternatively, an amidinium bond may be formed by attacking the amino group with methyl imidate esters.

Choice of Effector Molecules

Effector compounds used in the practice of the present invention are selected according to the purpose of the intended application (e.g., killing, prevention of cell proliferation, hormone therapy, or gene therapy). These compounds may include, for example, pharmaceutical agents, toxins, alkylating agents, enzymes, antibiotics, antimetabolites, anti-proliferative agents, hormones, neurotransmitters, DNA, radiopaque dyes, paramagnetic dyes, radioactive isotopes, fluorogenic compounds, marker compounds, compounds altering cell membrane permeability and insoluble matrices. The above is in no way intended to be an exhaustive list nor meant to limit the scope of the invention. Finally, a combination of compounds may be used. Examples of anticancer agents thay may be used to prepare prodrugs according to the invention include nucleoside analogues, cyclophosphamides and analogues, nitrosoureas, mitromycins, alkylating agents, alkaloids, bleomycin, anthracyclines and cisplatin and analogues.

A preferred example of anthracycline is doxorubicin, which may be conjugated to negatively charged residues via a cleavable spacer. Due to the presence of the negatively charged residues, the intact drug derivative is not taken up by the cells and cannot exert its intracellular cytotoxic activity. However, upon cleavage of the spacer (e.g. enzymatically) the negatively charged residues are removed and the drug derivative can enter the cells to exert its activity.

We designed a drug derivative which consists of the following parts:

a) the anti-cancer agent doxorubicin;
b) a chitin oligomer spacer conjugated to doxorubicin via its reducing terminus to the C13 carbonyl group of the drug; and
c) two taurine residues attached to two aldehyde groups generated at the nonreducing terminus of the chitin oligomer spacer by oxidation with periodate.

Doxorubicin belongs to the group of anthracycline drugs that have been extensively studied as antineoplastic agents for treating patients with cancer (Young and Ozols, 1981). Doxorubicin has a major role in the effective treatment of a variety of neoplastic diseases such as leukemia, breast cancer, and sarcomas. However, the successful use of doxorubicin has been hampered by conventional toxicities (hematopoietic suppression, nausea and vomiting, and alopecia) as well as unique toxicities (cardiomyopathy). Site-specific delivery of active doxorubicin molecules as outlined herein will greatly reduce the unwanted cytotoxic effects of the drug and, thereby, open up a whole new era in the use of this and other anthracyclines.

Chitin oligomers (oligomers of N-acetylglucosamine) were selected as spacers since chitin oligomers are susceptible to cleavage by human lysozyme (Holler et al, 1975a; Holler et al, 1975b). The selection of lysozyme offers several advantages for the proposed principle of therapy. First, lysozyme is abundant in mammalian secretions (saliva, tears, milk cervical mucus) and intracellularly in the lysosomes of tissues (in particular leukocytes and kidneys), but the lysozyme levels in serum are comparably low. As a result, unwanted cleavage of drug derivatives in the circulation will be limited. Second, there is no naturally circulating substrate for lysozyme that could compete with the drug derivatives for the active sites of the targeted enzyme molecules.

To prevent the cellular uptake of the drug derivative, two sulfonic acid residues are attached to the carbohydrate space. The inhibitory effect of negatively charged sulfonic acid groups on the cellular uptake of small molecular weight compounds is well documented for a variety of molecules, such as Trypan blue used for dye exclusion tests (Phillips, 1973) or Evans blue used as a diagnostic aid for blood volume determinations in man (The Merck Index, ninth edition, 1976).

BRIEF DESCRIPTION OF THE FIGURES

FIG. 3. Immunoreactivity of the 16.88-lysozyme conjugate.

EXAMPLE 1

Preparation of Antibody-Enzyme Conjugates Using the Enzyme Lysozyme and Human Monoclonal Antibody 16.88

Derivatization of Human Monoclonal Antibody 16.88 with Pyridyl Disulfide Groups

The following experiments demonstrate the formation of a pyridyl disulfide derivatized antibody in conjugation to sulfhydryl-derivatized lysozyme (activator). Rather than destabilize the antibody by reducing interchain or intrachain disulfide bridges to generate sulfhydryl groups to couple to lysozyme, multiple activated disulfide groups are introduced into the antibody using N-succinimidyl-3-(2-pyridyldithio)propionate (SPDP).

Alternative linkers may be used in the event that an antibody loses immunological activity when derivatized with SPDP. A new linker S-(2,thiopyridyl)-L-cysteine hydrazide (TPCH) (Zara et al, 1989) has been described. TPCH introduces a linker with a terminal reactive pyridyl disulfide residue coupled to oxidized carbohydrate residues of the antibody. TPCH may allow introduction of more spacer groups without impairing the antibody function than linkers coupling through antibody epsilon amino groups such as SPDP. Mixed together, the sulfhydryls introduced into the activator enzyme with 2-iminothiolane (2-IT) react with pyridyl disulfide residues introduced into the antibody with SPDP or TPCH to form a disulfide bond. Studies with antibody-toxin conjugates linked via disulfide bonds (Thorpe et al 1987) suggest that the disulfide bond between the antibody and the activator enzyme may be partially unstable in vivo resulting in the release of the activator enzyme from the antibody prior to localization in the tumor. This could be prevented by linking the antibody and activator using a more stable thioether bond introduced by using a cross-linking reagent such as N(gamma-maleimidobutyryloxy)succinimide (GMBS) in place of SPDP or TPCH. GMBS introduces a terminal reactive malemide group, rather than a sulfhydryl, to form a more stable thioether linkage with the sulfhydryl introduced into lysozyme with 2-IT.

In the example presented the antibody is the human IgM anti-tumor monoclonal antibody 16.88 (Haspel et al, 1985) which reacts with an antigen (CTA#1) found in the cytoplasm of certain types of carcinoma cells including carcinomas of the colon, breast, ovary, pancreas, and lung. Pyridyldisulfide residues were introduced by two different procedures.

Figures 1, 10:
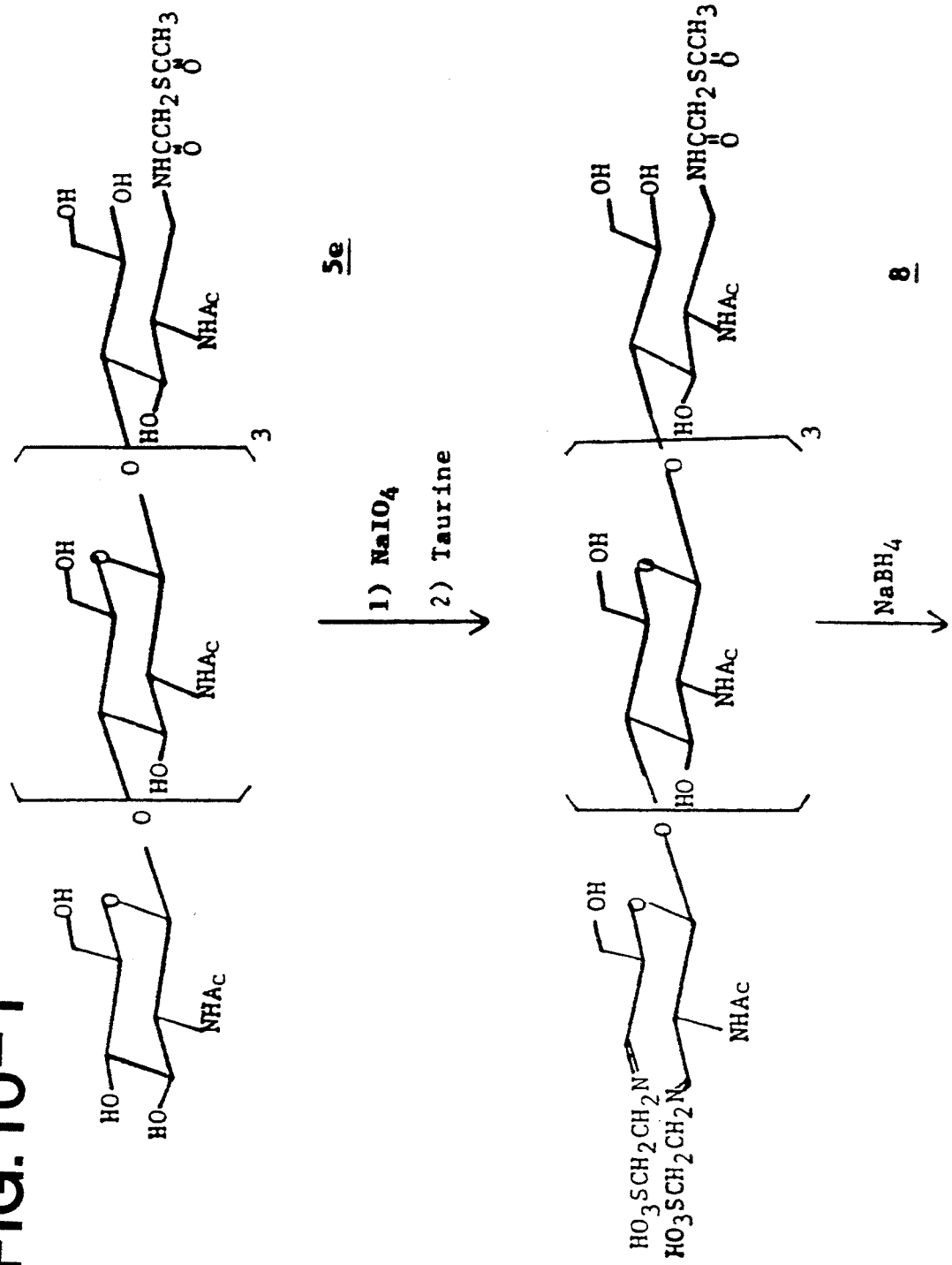
FIG. 1. Immunoreactivity of SPDP-modified 16.88.
FIG. 10. Attachment of taurine residues to thioester-derivatized chitin oligomers.

Procedure A: Antibody 16.88 was derivatized at the amino groups of lysine residues using the heterobifunctional linker N-succinimidyl-3-(2-pyridyldithio)propionate (SPDP). Eight moles SPDP could be incorporated per mole 16.88 with an acceptable reduction of 16.88 antibody activity (FIG. 1). To obtain the 8:1 incorporation ratio, 10 moles SPDP were reacted with each mole 16.88 for 30 minutes at room temperature in 0.01M phosphate buffer pH 7.0 containing 0.1M sodium chloride. Conjugated antibody was separated from excess SPDP by gel filtration on Sephadex G-25. Immunoreactivity was assessed in comparison to an unmodified 16.88 reference by comparing the ability of the SPDP modified and unmodified 16.88 reference to compete with I-125 labeled unmodified 16.88 reference in binding to cognate antigen, CTA#1. At an incorporation ratio of 8.6:1 the amount of SPDP-16.88 required to reduce binding of $^{125}$I-16.88 by 50% was increased by a factor of 4.

Figures 2, 10:
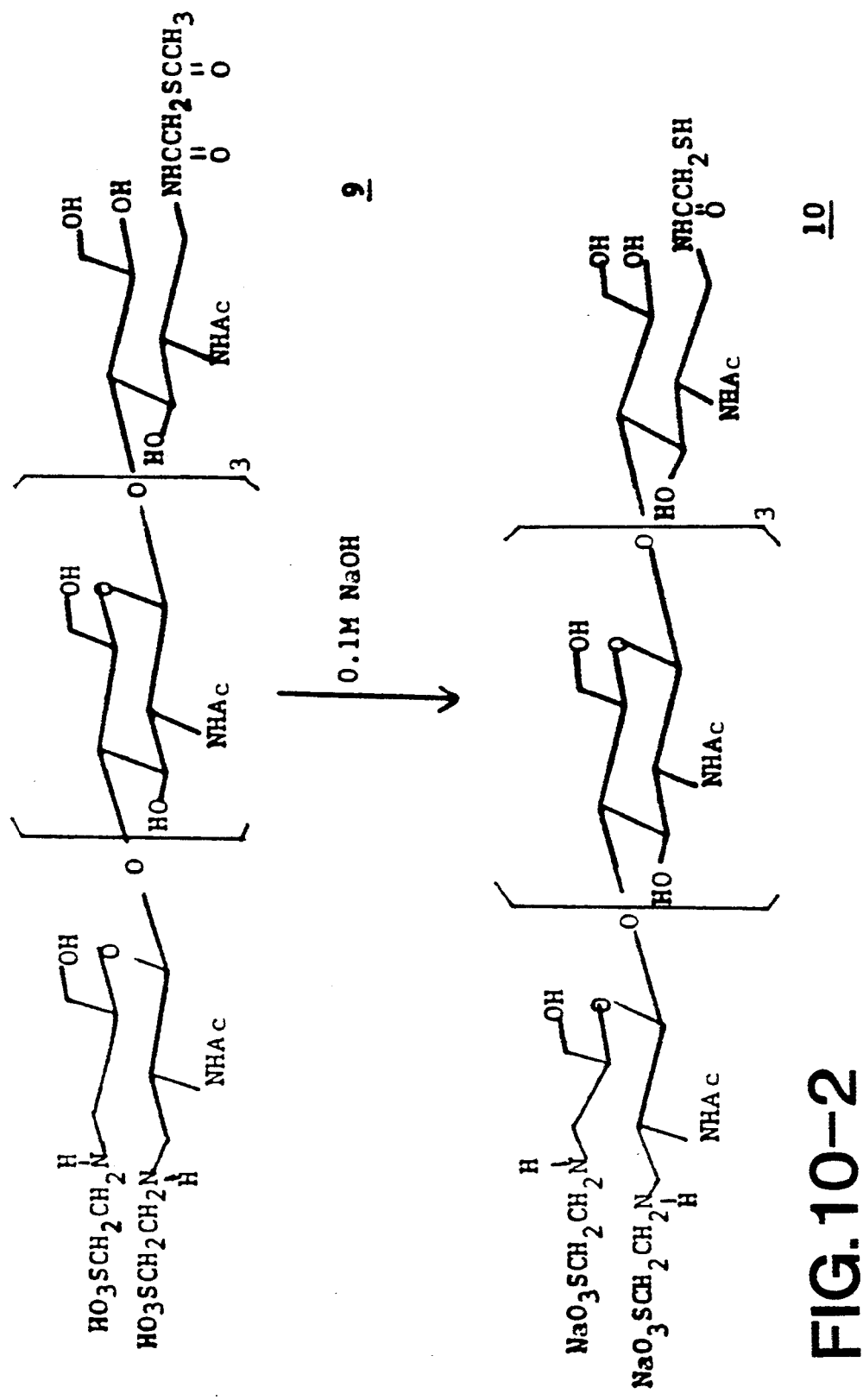
FIG. 2. Immunoreactivity of TPCH modified 16.88.

Procedure B: Carbohydrate moieties of 16.88 were oxidized to generate aldehyde functions to which were attached the hetero-bifunctional linker S-(2-thiopyridyl)-L-cysteine hydrazide (TPCH). Unlike SPDP which links to antibody via amino groups on the protein, the hydrazide moiety of TPCH forms hydrazones with aldehyde groups generated in the carbohydrate components of 16.88 by mild periodate oxidation. As shown in FIG. 2 incorporation of as many as 17 moles TPCH per mole 16.88 could be achieved with no detectable loss of antibody activity.

Derivatization of 16.88 was performed by reacting a solution of 16.88 at 2 mg/ml concentration in 0.1M sodium acetate buffer pH 5.5 with 10 mM sodium periodate at 4° C. for 10 minutes. TPCH was added at a ratio of 7000 moles TPCH/mole 16.88 (corresponds to an approximately 20-fold molar excess of TPCH with respect to primary amino groups of 16.88) in 0.1M sodium acetate buffer, pH 5.5. Excess TPCH was removed by gel filtration in Sephadex G-25 in 0.01M phosphate buffered pH 7.0 containing 0.1M sodium chloride.

Immunoreactivity of the derivatized antibody was assessed by competitive binding analysis. Derivatized and native 16.88 antibody were compared in their ability to compete with radiolabeled native 16.88 antibody for binding to specific antigen. ID$_{50}$ values for derivatized and native antibody were compared.

Derivatization of Lysozyme

Lysozyme amino groups may be derivatized with amino-reactive heterobifunctional reagents for coupling to 16.88. Amino group derivatization was investigated with SPDP, GMBS, and 2-IT. Boh SPDP and GMBS severely compromised enzyme activity even at incorporation ratios as low as 2 linker molecules/lysozyme (Table 1). Derivatization with 2-IT at the ratio of 2 linker molecules/lysozyme resulted in retention of 60-68% of the lysozyme activity.

Lysozyme was derivatized with a 100-fold molar excess of 2-IT in 0.01M phosphate buffer pH 8.0 containing 0.1M sodium chloride and 0.001M dithiothreitol for 10 minutes at room temperature. The reaction was stopped by addition of a 10-fold molar excess (to 2-IT) of ethanolamine. Derivatized lysozyme was removed from excess 2-IT and ethanolamine by gel filtration chromatography on Sephadex G-10 in the same buffer at pH 7.0 containing 2mM ethylenediaminetetraacetic acid and immediately used for coupling to pyridyl disulfide-derivatized 16-88 antibody. Lysozyme activity was measured using a *Micrococcus lysodeikticus* suspension (Shugar, 1949).

TABLE 1

| The Effect of Lysozyme Modification on Enzyme Activity | | |
|---|---|---|
| Heterobifunctional Linker | Molar Ratios (linker:lysozyme) | Remaining Lysozyme Activity (%) |
| | | Exp I.    Exp II. |
| 2-iminothiolane | 2.1:1 | 60%    68% |
| SATA | 2.0:1 | 10% |
| GMBS | 1.8:1 | 5%    18% |

*As measured by the *Micrococcus Lysodeikticus* Assay (Shugar, 1949).

Synthesis of 16.88-Lysoze Conjugates.

2-IT-derivatized lysozyme was coupled to SPDP-derivatized 16.88 (Procedure A) or to TPCH- derivatized 16.88 (Procedure B).

Procedure A: 16.88-SPDP and 2-IT-derivatized lysozyme were coupled by mixing the two components at a 1:1 (w/w) ratio. The solution was flushed with nitrogen gas during the 24–48 hour coupling reaction at 4° C. The 16.88-lysozyme was separated from free lysozyme by gel filtration on Fractogel 55F in 0.01M phosphate buffer (pH 7.0) with 0.1M sodium chloride.

Procedure B: 2-IT-derivatized lysozyme was mixed with TPCH-derivatized 16.88 at a 1:1 (w/w) ratio and reacted overnight at room temperature. 16.88-lysozyme was separated from free lysozyme by gel filtration as in Procedure A.

Comparison of coupling yields between SPDP-derivatized 16.88 and TPCH-derivatized 16.88 indicated a higher overall yield with the SPDP modified antibody. Routinely 3 to 4 moles of lysozyme could be coupled per mole SPDP modified 16.88. Antigen binding activity of the 16.88-lysozyme conjugate was measured in the competitive binding assay with respect to an unmodified 16.88 reference. The results shown in FIG. 3 indicate no further loss of antibody activity in the 16.88-lysozyme conjugate compared to SPDP modified 16.88 as shown in FIG. 1.

Figure 4:
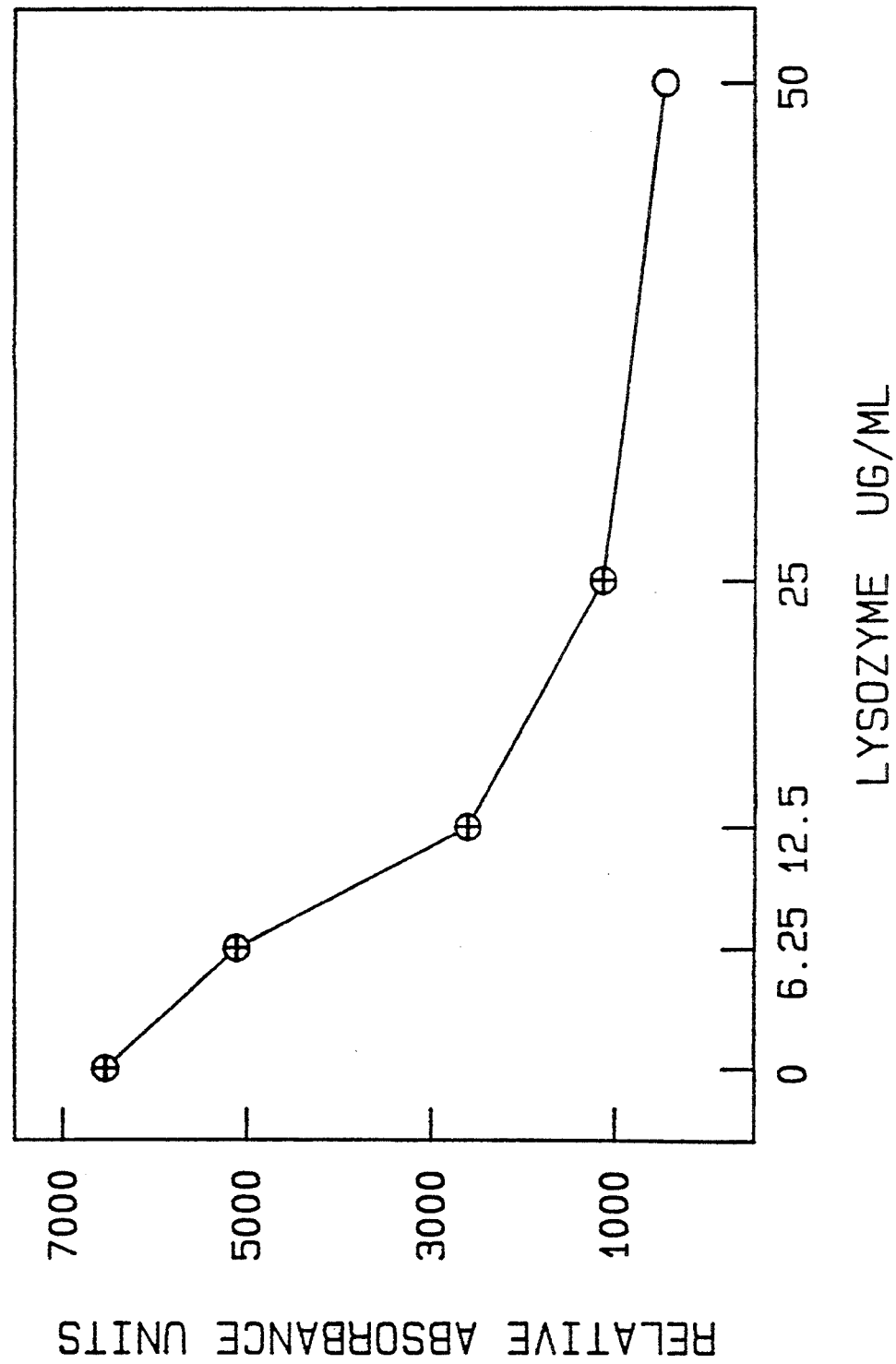
FIG. 4. Standard curve: Lysozyme Activity.

Enzymatic activity of the conjugates was measured with a novel assay using a soluble substrate similar to the prodrug. The assay substrate was an N-acetyl glucosamine pentamer $(GlcNAc)_5$ (1 mM) in 0.005M citrate buffer pH 4.5. Digested $(GlcNAc)_5$ was separated from the substrate after 4 hours at 37° C. by thin layer chromatography on silica using a 2-propanol/water/ammonium hydroxide (62/37/1) solvent system. $(GlcNAc)_5$ and digested substrate were visualized by spraying with 10% sulfuric acid in ethanol. Quantitation was obtained by scanning densitometry. The method measures lysozyme activity over a range of 6.25 to 50 μg/ml concentration. The standard curve (FIG. 4) indicated that the assay is most sensitive in the range 6.25 to 10 μg/ml lysozyme concentration. Table 2 shows that 16.88-lysozyme has approximately 90% of the activity of an equal amount of 2-IT-derivatized lysozyme.

Stability of 16.88-lysozyme has been monitored under 4° C. and room temperature (25° C.) storage conditions. The results (Table 3) indicate no significant loss of lysozyme activity over a period of one month at 4° C. or at 25° C. A 54% reduction in 16.88 antibody activity at room temperature and 33% loss of antibody activity at 4° C. was seen after one month's storage.

TABLE 2

The Effect of Antibody Coupling on Lysozyme Activity

| Lysozyme-Derivative | Molar Ratios (Lysozyme:16.88) | Remaining Lysozyme Activity (%) |
|---|---|---|
| lysozyme-IT | | 100 |
| lysozyme-16.88 | 4:1 | 92 |
| | 3:1 | 90 |

TABLE 3

Stability of Lysozyme-16.88 Immunoconjugates

| | μg of Antibody Needed for 50% Inhibition of Binding | | Remaining Lysozyme Activity (%) | |
|---|---|---|---|---|
| Date | 25° C. | 4° C. | 25° C. | 4° C. |
| 10/13/89 | 6 μg (100%) | 7 μg (100%) | 100% | 100% |
| 11/13/89 | 13 μg (46%) | 10.5 μg (67%) | 90% | 106% |

Figure 5:
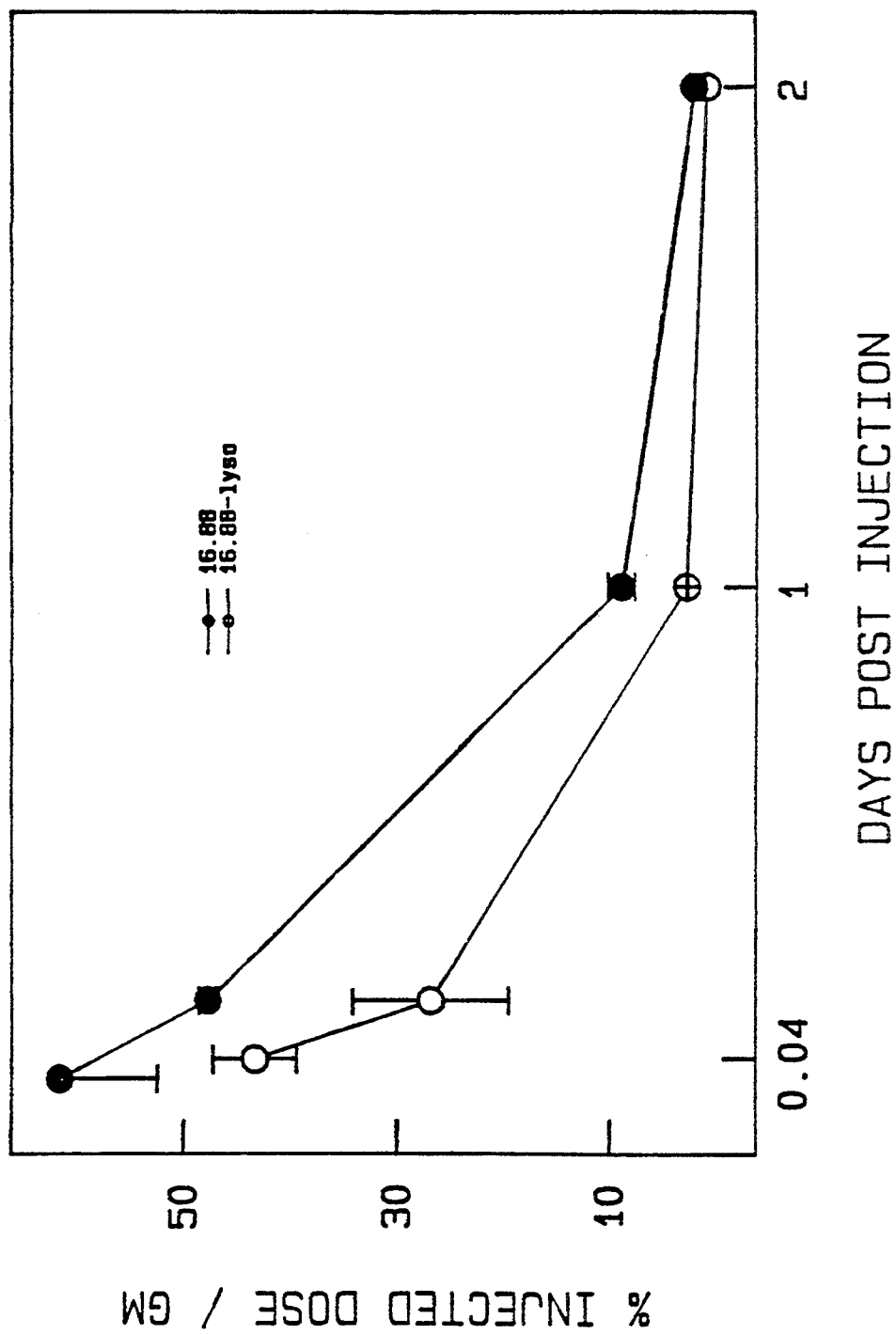
FIG. 5. Serum retention of 16.88 lysozyme in tumor xenograft bearing nude mice.
Figure 6:
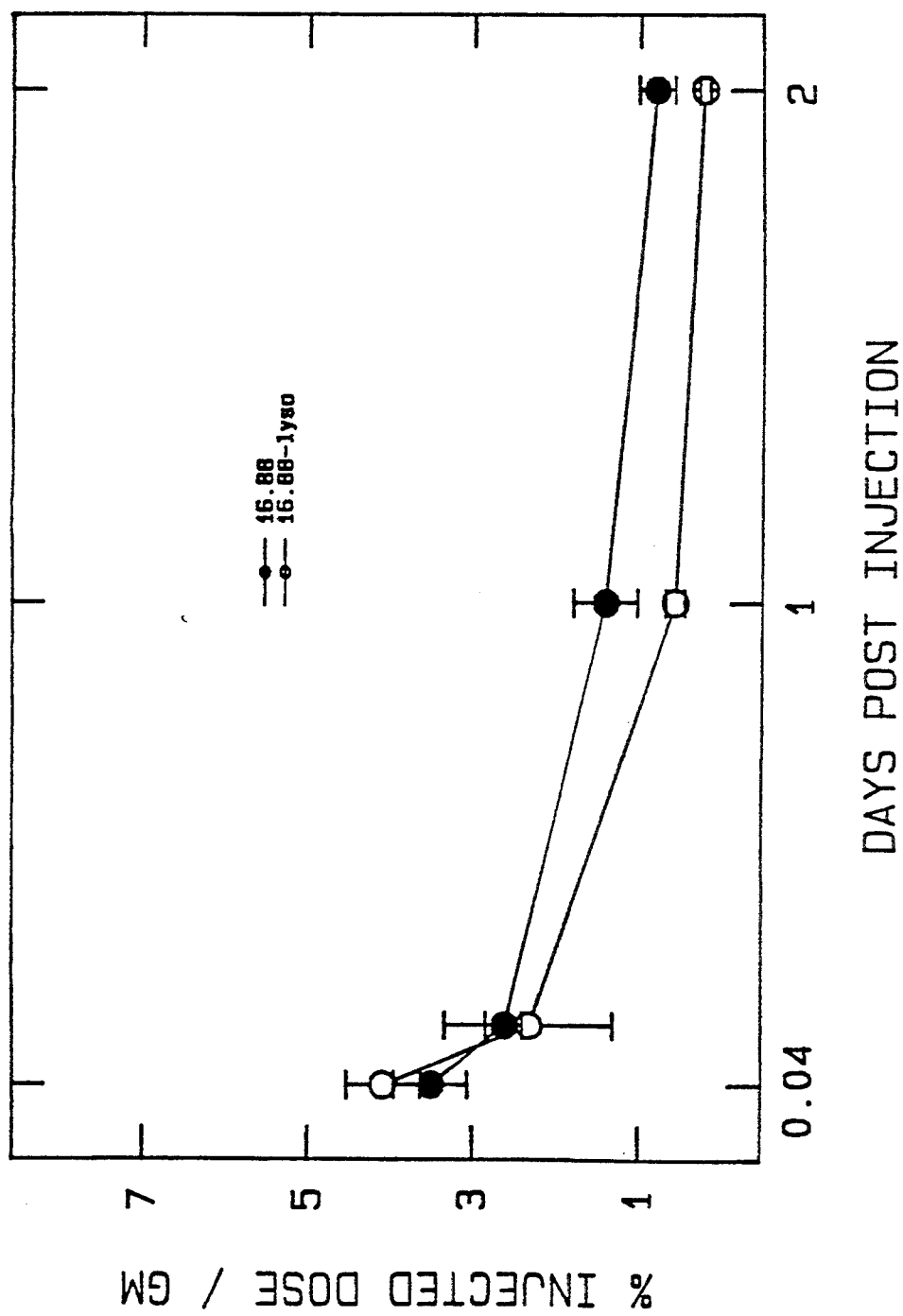
FIG. 6. Tumor retention of 16.88-lysozyme in tumor xenograft bearing nude mice.

In vivo Tumor Localization and Pharmacokinetics of 16.88-Lysozyme in a Nude Mouse Human Colon Tumor Xenograft Model 16.88-lysozyme or 16.88 radiolabeled with I-125 to a specific activity at 1 mci/mg was injected intravenously (50 mCi, 50 μg) into groups of 15 Balb/c athymic nude mice bearing 0.2 gram subcutaneous human colon tumor xenografts. The colon tumor (THO) expresses the antigen recognized by human monoclonal antibody 16.88. The purpose was to compare the antibody-lysozyme (1:4) conjugate and the unconjugated 16.88 antibody to assess the effects of lysozyme on the normal tumor uptake and serum (blood) retention of the antibody. Serum retention (FIG. 5) was approximately the same for 16.88-lysozyme and 16.88 over the period of four hours to two days post-injection, with 16.88 exhibiting a serum half-life of 12.4 hours and 16.88-lysozyme a serum half-life of 11.8 hours. From the time of injection to one hour post-injection, 16.88-lysozyme appeared to clear more quickly from the serum. The amounts of 16.88-lysozyme or 16.88 in the tumor xenograft was at a maximum one hour post-injection; 4% for 16.88-lysozyme, 3.5% for 16.88. Both 16.88-lysozyme and 16.88 had rates of clearance from the tumor that were similar from one hour to two days post-administration (FIG. 6).

EXAMPLE 2

Preparation of the Doxorubicin Derivative

The drug derivative consists of the following parts:
a) doxorubicin;
b) a chitin oligomer spacer conjugated to doxorubicin via its reducing terminus to the $C_{13}$ carbonyl group of the drug;
c) two taurine residues attached to two aldehyde groups generated at the non-reducing terminus of the chitin oligomer spacer by oxidation with periodate.

Derivatization of Doxorubicin With a Pyridyl Disulfide Residue

Figure 7:
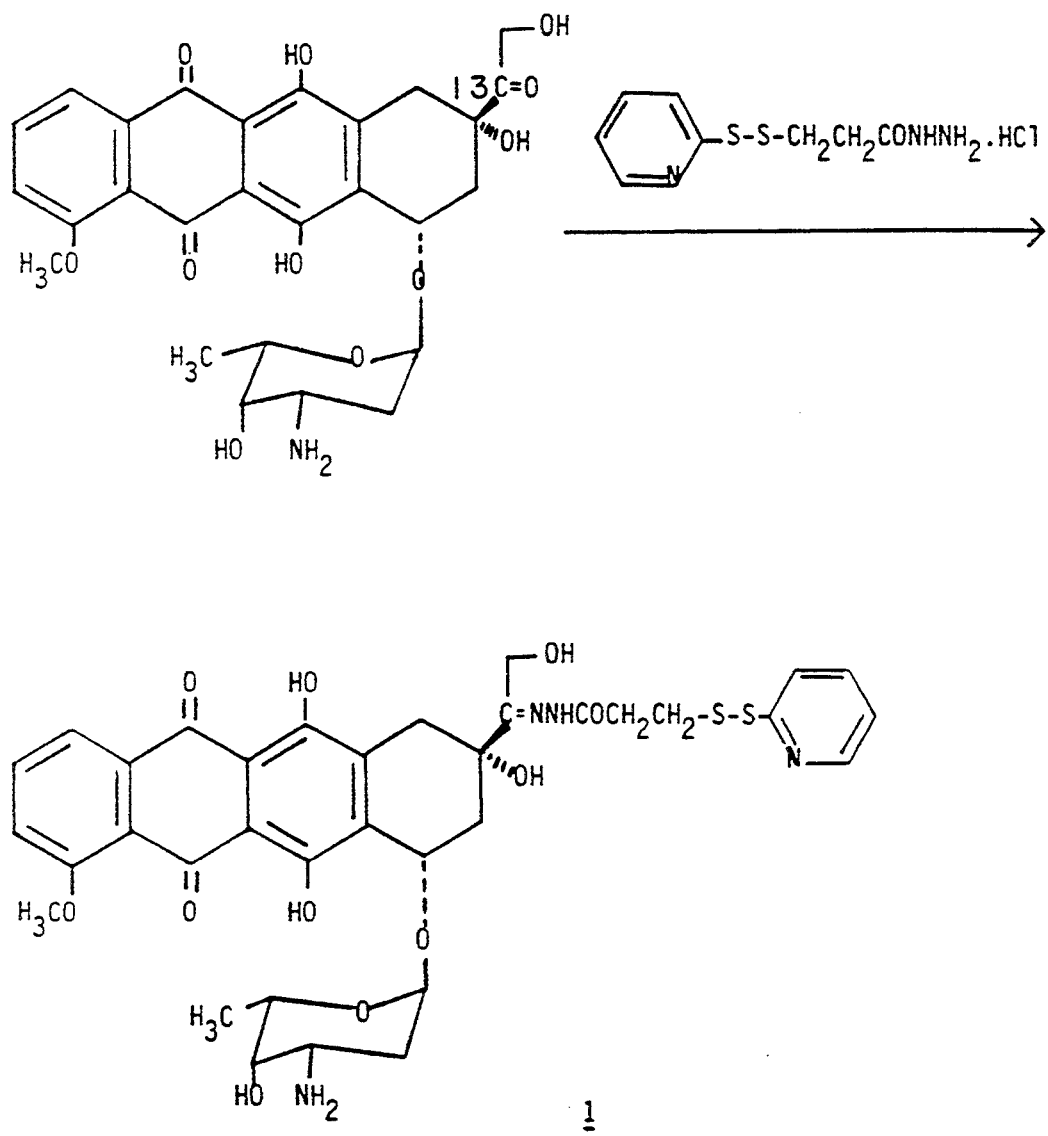
FIG. 7. Derivatization of doxorubicin with a pyridyl disulfide residue.

For coupling doxorubicin to the reducing terminus of the chitin oligomer spacer, the molecule is modified at its C13 carbonyl group with a hydrazide derivative according to published procedures (Hurwitz et al, 1980; Hurwitz et al, 1983). The hydrazide derivative used in this example is a heterobifunctional reagent containing one hydrazide moiety and one pyridyl disulfide moiety (FIG. 7). The synthesis of the hydrazide derivative [3-(2-pyridyldithio)propionic acid hydrazide (PDPH)] is performed in a three step procedure: preparation of the pyridyl disulfide derivative of 3-mercapto-propionic acid, condensation of the carboxyl group with t-butyl carbazate, followed by deprotection with ethyl acetate saturated with HCl.

A solution of 58 mg (0.1 mmole) of doxorubicin-HCl in 0.85 ml of $H_2O$ was treated with a solution of 380 mg (1 mmole) of PDPH and 84 mg (1.02 mmole) of NaOAc in 0.6 ml of water. To this clear red solution was added 4.8 ml of 0.1M $Na_2CO_3$ and stirred at room temperature (RT) overnight. The reaction mixture was extracted with $CHCl_3/MeOH(3/1)$, the combined extract evaporated and purified by preparative TLC (Tapered Preparative Uniplate-T, $CHCl_3/MeOH/N-H_4OH=90/10/1$) to give compound 1. FAB-MS; m/z=755(M+1).

Figure 8:
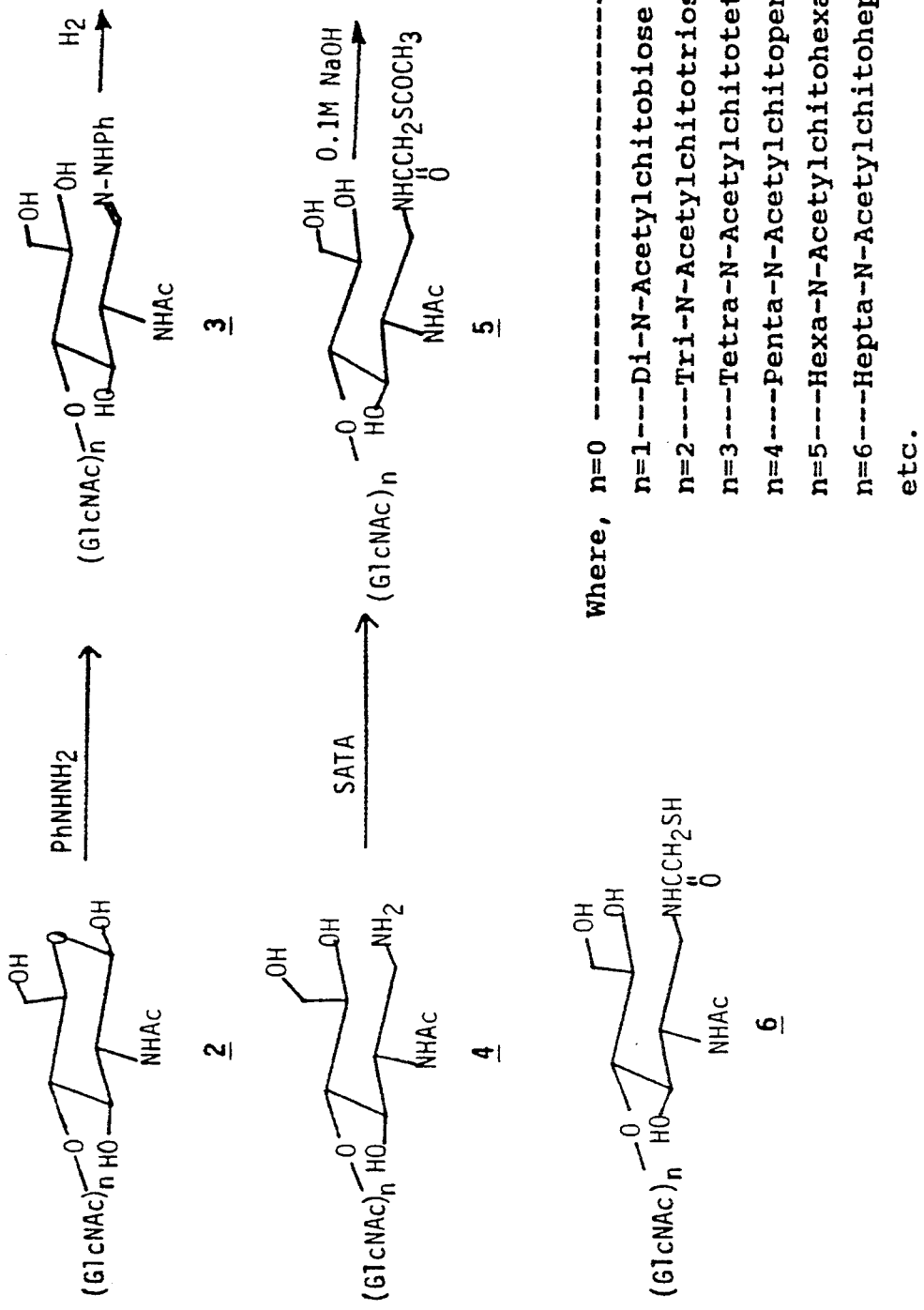
FIG. 8. Preparation of thioester-derivatized chitin oligosaccharides.

Preparation of Thioester-Derivatized Chitin Oligosaccharides (FIG. 8)

Chitin was hydrolyzed by the method developed by Rupley (1964) and purified through a P2 gel filtration column. Chitin oligo-saccharides thus obtained were derivatized as shown in FIG. 8. Penta-N-acetyl-chitopentaose (2e) serves as an example. A mixture of 0.44 g (0.42 mmole) of penta-N-acetylchitopentaose (2e) in 10 ml of water, 8 ml of ethanol, and 1 ml of phenylhydrazine was heated to 125° C. for two days. The reaction mixture was cooled to RT, 20 ml of water added, and extracted with ether (25 ml×3). The aqueous layer was lyophilized and the product was further purified through a reverse phase column (C18) (40% MeOH/$H_2O$). The compound 3e (0.33 g, 0.29 mmole) was dissolved in water (20 ml), ¼ teaspoon of Raney Nickel W-2 was added, and hydrogenated on a Parr apparatus overnight. The reaction mixture was filtered through a Celite bed, concentrated, and charged onto a Dowex 50-WX2 (H+) ion exchange column. The column was first eluted with 80 ml of water followed by 50 ml of 2N-$NH_4OH$. The elute was lyophilized to give 0.15 g of compound 4e. The compound 4e (0.15 g, 0.15 mmole) was dissolved in water (5 ml), mixed with 0.067 g (0.29 mmole) of SATA in 0.8 ml of DMF, and stirred at RT overnight. The reaction mixture was diluted with water (20 ml), extracted with chloroform (20 ml×3), and lyophilized to give compound 5e which was hydrolyzed with 10 ml of 0.1M NaOH at RT for two hours and lyophilized to give a yellowish powder 6e.

Figure 9:
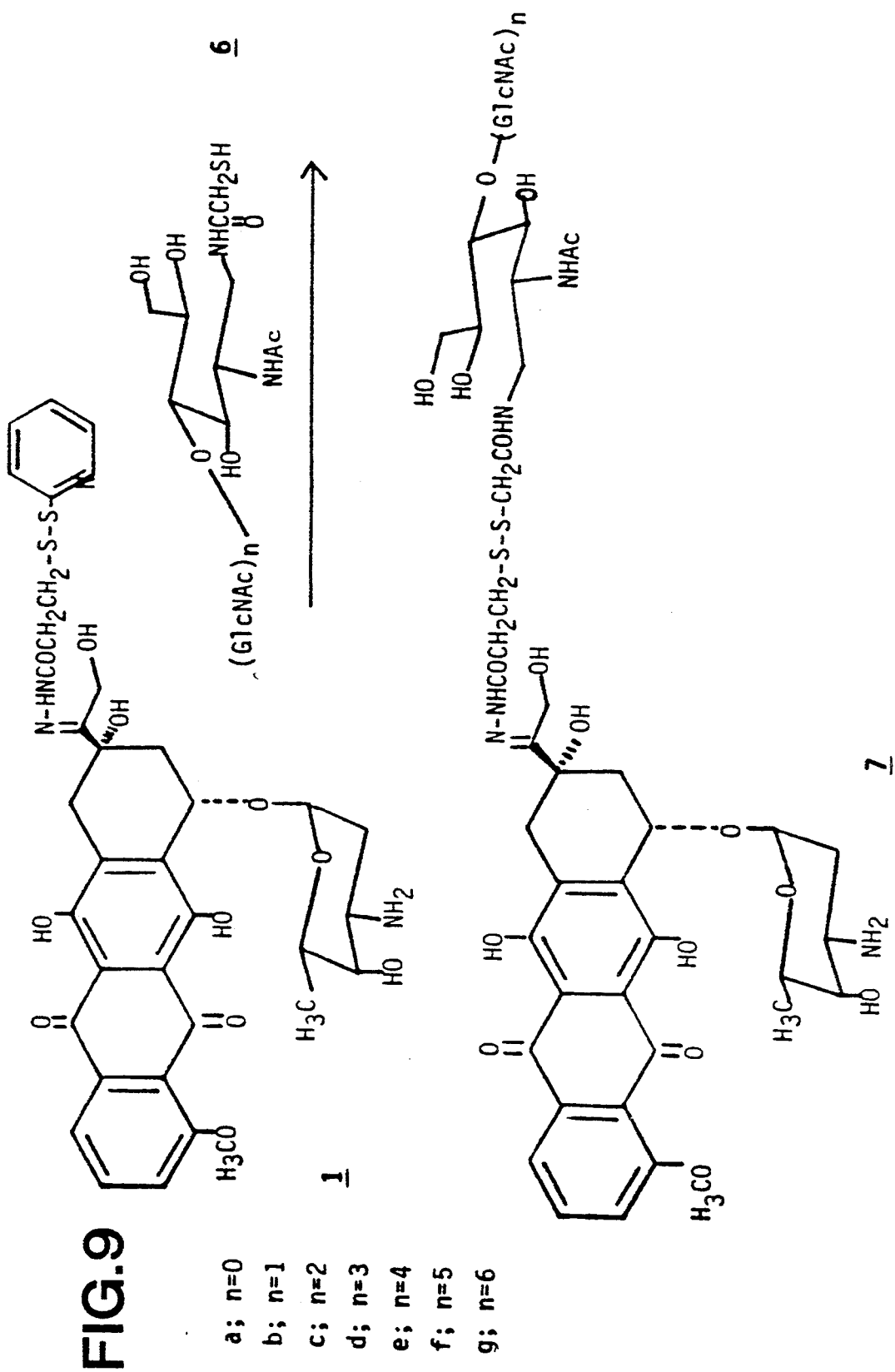
FIG. 9. Attachment of thioester-derivatized chitin oligomers to pyridyl disulfide-derivatized doxorubicin.

Attachment of Thioester-Derivatized Chitin Oligomers to Pyridyl Disulfide-Derivatized Doxorubicin (FIG. 9)

The PDPH-derivatized doxorubicin 1 (0.01 g, 0.013 mmole) was dissolved in ethanol (12 ml), catalytic amount of HOAc followed by 0.25 g (0.023 mmole) of compound 6e were added, and stirred overnight at RT. The solvent was evaporated and the residue was dissolved in water (10 ml), extracted with $CHCl_3/MeOH=7/3$ and the combined extracts were evaporated to give a dark brown powder, 7 [TLC showed no detectable amount of thioester-derivatized chitin oligomer (6e). Silica gel, 2-propanol/water/$N H_4OH=72/27/1$].

Attachment of Taurine Residues to Thioester-Derivatized Chitin Oligomers (FIG. 10)

Oxidation of the thioester-derivatized chitin oligomer with $NaIO_4$ formed dialdehydes at the non-reducing terminus which were reacted with taurine to form a Schiff's base (8). Compound 8 was reduced to a more stable amine with $NaBH_4$ to give compound 9. Hydrolysis of compound 9 with 0.1M NaOH formed the derivatized chitin oligomer spacer containing a free sulfhydryl at the reducing terminus (10).

Preparation of the Doxorubicin Derivative Containing Taurine Residues via a Cleavable Chitin Oligomer Spacer The doxorubicin derivative containing a chitin oligomer via a disulfide linkage (7) was subjected to mild $NaIO_4$ treatment at pH 6.0 for 60 minutes at RT. After quenching excess $NaIO_4$ with ethylene glycol, a 10-fold molar excess of taurine (with respect to the doxorubicin derivative) was added to the reaction mixture. After an additional incubation for one hour at RT the derivative was used in cytotoxicity assays after adjustment to pH 7.2. Conversion of compound 7 to the taurine derivative was confirmed by TLC analysis on silica (2-propanol/water/$NH_4OH=72/27/1$.

Figure 11:
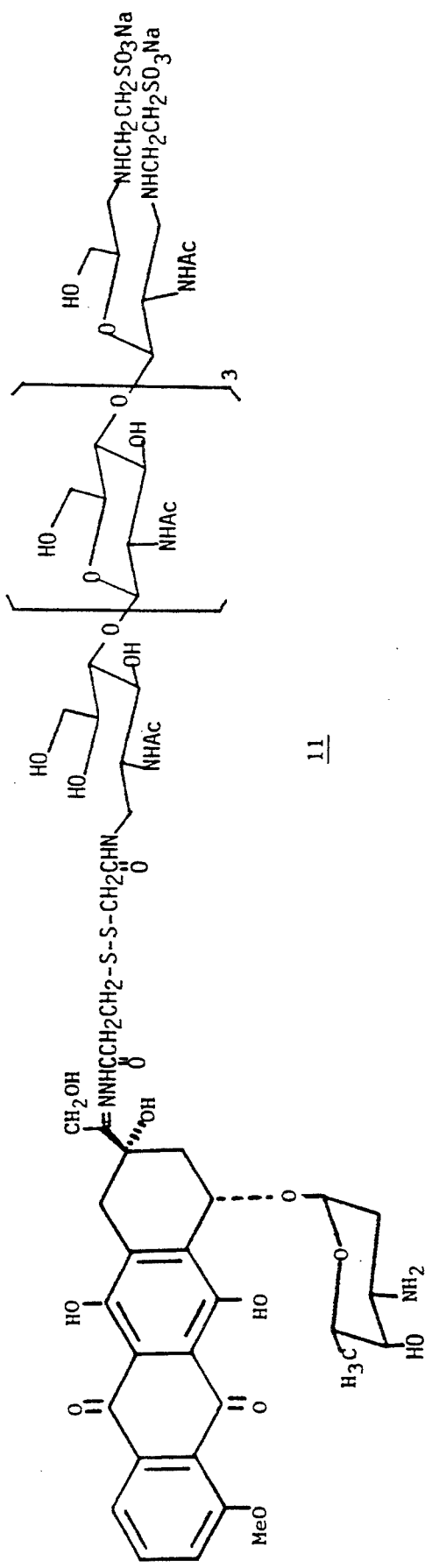
FIG. 11. Doxorubicin derivative containing taurine residues via a cleavable chitin oligomer spacer.

An alternative synthesis procedure allows preparation of a more stable drug derivative using the chitin spacer shown in FIG. 10. Pyridyldisulfide-derivatized doxorubicin (1) is reacted with taurine-derivatized chitin oligomer containing a free sulfhydryl group at the reducing terminus (10) to form the doxorubicin derivative (11) shown in FIG. 11.

Number of Sulfonic Acid Residues Per Doxorubicin Derivative

If required, the number of sulfonic acid residues per drug derivative can easily be changed. For example, four sulfonic acid residues instead of two can be coupled per drug derivative by using hydrazide derivatives, each carrying two sulfonic acid residues. Furthermore, the introduction of negatively charged groups is not restricted to sulfonic acid residues. For example, phosphates or phosphonic acid residues (e.g., 3-aminopropylphosphonic acid) may also be used.

Length of Chitin Oligomer Spacer in the Prodrug

The relative rate of cleavage of chitin oligomers by lysozyme is proportional to the length of the chain. For example, chitohexaose is cleaved at a 30,000 fold higher rate than chitotriose (Imoto et al, 1972). Therefore, chitin oligomer spacers larger than pentamers can be expected to form drugs more readily activated by lysozyme.

Figure 12:
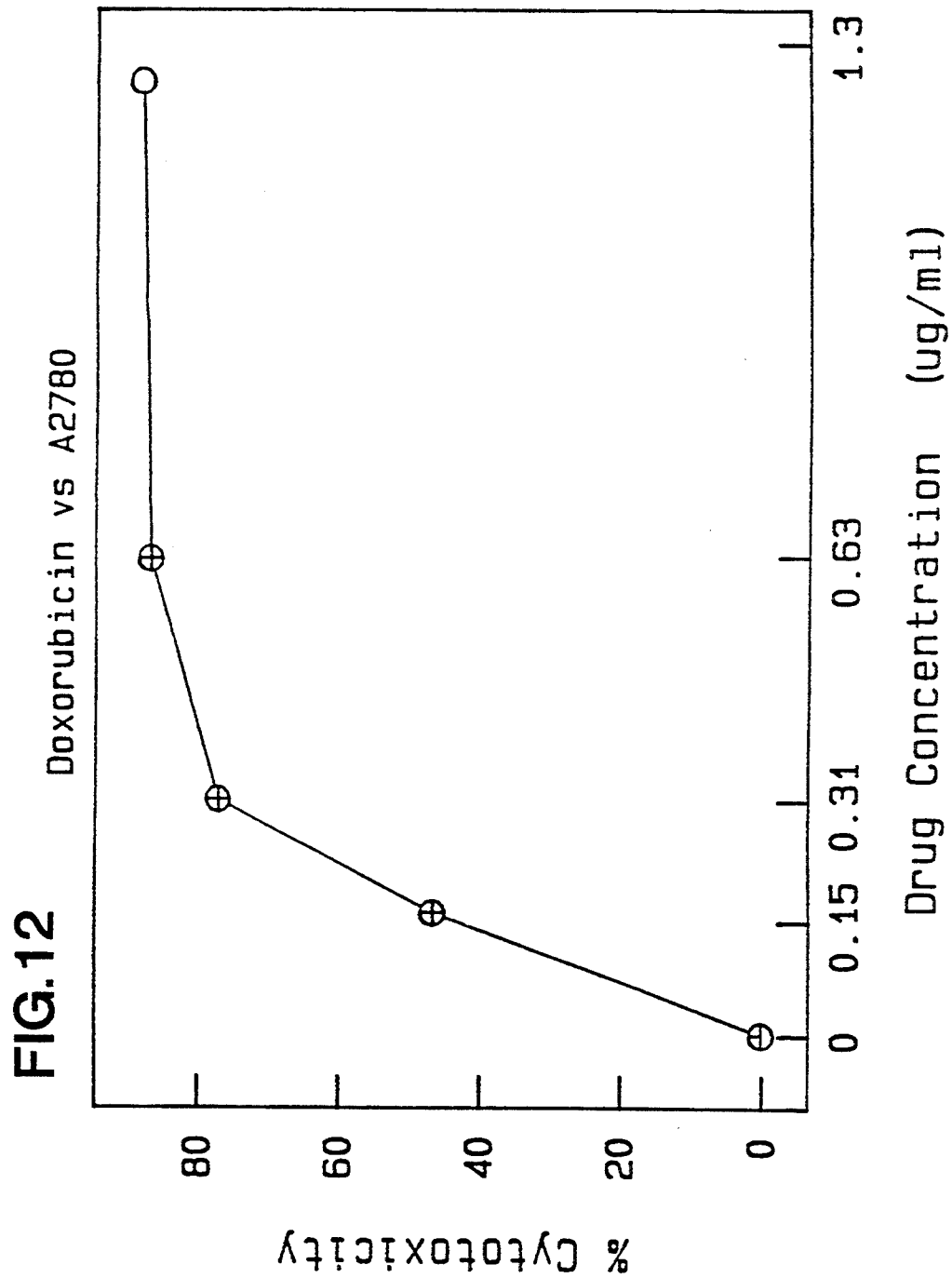
FIG. 12. Dose response of doxorubicin vs. A2780 ovarian carcinoma cells.

Cytotoxic Activity of Doxorubicin Derivatives Containing Chitin Oligosaccharides of Various Lengths In vitro cytotoxicity was measured using inhibition of $^3H$-thymidine uptake with A2780 ovarian carcinoma cells. Briefly, 0.1 ml of a suspension of $2\times10^4$ cells in Eagle's modified minimal essential medium were added to the wells of a 96-well microculture plate. Volumes (0.1 ml) of doxorubicin or a doxorubicin-derivative at concentrations of 0.6 to 10 µg/ml were added in quadruplicate and the mixtures were incubated for 4 hours at 37° C. in a humidified $CO_2$ incubator. 0.1 ml $^3H$-thymidine (10 µCi/ml) were added to each well and incubated for 16 hours. Thereafter, the cells were washed, harvested with 0.5N sodium hydroxide and counted for incorporation of $^3H$-thymidine. FIG. 12 shows the results of a typical assay with doxorubicin. Table 4 compares the activity of doxorubicin modified with the linker (PDPH) used to couple $(GlcNAc)_n$, and doxorubicin coupled to $(GlcNAc)_1$ or $(GlcNAc)_5$. Regardless of the extent of modification of the doxorubicin there was no detectable loss of drug activity. This result indicates that the drug produced by the action of lysozyme is as cytotoxic as native doxorubicin.

TABLE 4

| Cytotoxicity of Doxorubicin Derivative | |
|---|---|
| Derivative | % Cytotoxicity* |
| Dox-PDPH | 67.1 |
| Dox-(GlcNAc)$_1$ | 99.6 |
| Dox-(GlcNAc)$_5$ | 100.0 |

Figure 13:
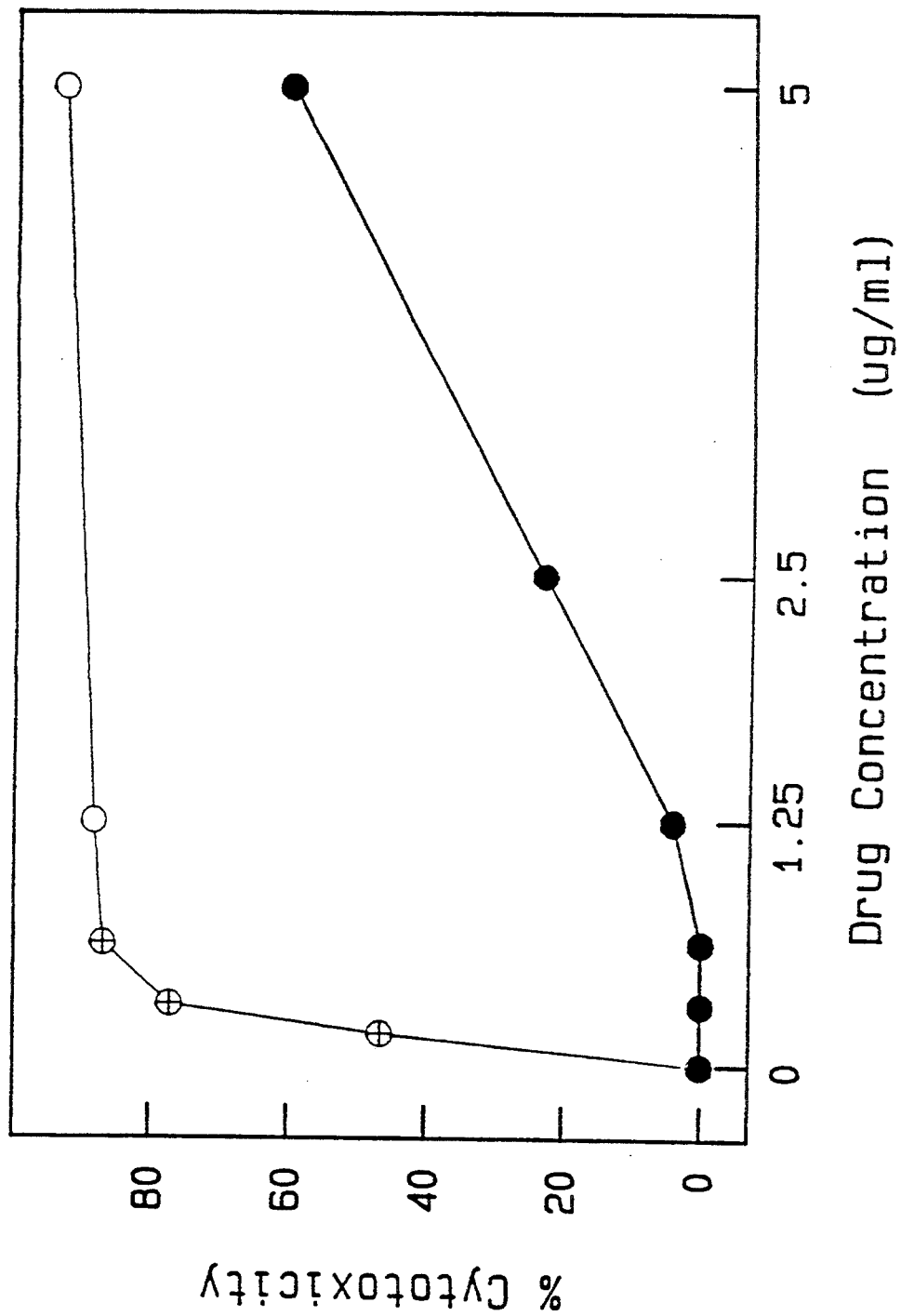
FIG. 13. Cytotoxic activity of a doxorubicin derivative containing taurine residues via a cleavable chitin oligomer spacer.

*% cytotoxicity compared to doxorubicin. Drug concentration equal to 0.625 µg/ml Cytotoxic Activity of a Doxorubicin Derivative Containing Taurine Residues via a Cleavable Chitin Oligomer Spacer FIG. 13 shows the cytotoxic activity of the doxorubicin derivative containing taurine residues in comparison to that of a doxorubicin derivative containing a chitopentaose spacer without attached taurine residues. Cytotoxicity was performed as previously described. The taurine containing drug was approximately 20-fold less cytotoxic. Exposure of the chitin oligomer spacer with attached taurine residues to lysozyme resulted in cleavage of the spacer as confirmed by TLC (2-propanol/water/$NH_4OH=67/32/1$). These data indicate that the taurine-containing prodrug can be converted into active drug species containing chitin oligomers of various length, which are as active as the parent drug (Table 4).

REFERENCES

Bagshawe, K. D. Antibody Directed Enzymes Revive Anti-Cancer Prodrugs Concept. Br. Med. J. 56, 531–537 (1987). Briggs, R. S., Perillie, P. E. and Finch, S. C. Lysozyme in Bone Marrow and Peripheral Blood Cells. J. Histochem. Cytochem. 14, 167–170 (1966).

Ellman, G. L. Tissue Sulfhydryl Groups. Arch. Biochem. Biophys 87, 70–79 (1959).

Flanagan, P. and Lionetti, F. Lysozyme Distribution in Blood. J. Hematology 10, 497–501, 1955.

Flickinger R. A. and Trost, S. R. Cytotoxicity of Antibody Phospholipase C Conjugate on Cultured Friend Leukemia Cells. Eur. J. Cancer 12, 159–160 (1976).

Gallego, J., Price, M. R. and Baldwin, R. W. Preparation of Four Daunomycin-Monoclonal Antibody 79IT/36 Conjugates with Anti-Tumor Activity. Int. J. Cancer 33, 737–744 (1984).

Hamm, C. W., Kupper, W., Bredehorst, R., Hilz, H., Bleifeld, W. Quantitation of Coronary venous Adenosine in Patients: Limitations Evaluated by Radioimmunoassay. Cardiovascular Res. 22, 236–243 (1988).

Haspel, M. V., McCabe, R. P., Pomato, N., Janesch, N. J., Knowlton, J. V., Peters, L. C., Hoover, H. C., Jr. and Hanna, M.G., Jr. Generation of Tumor Cell-Reactive Humor Monoclonal Antibodies Using Peripheral Blood Lymphocytes from Actively Immunized Colorectal Carcinoma Patents. Cancer Res. 45:3931–3961, 1985.

Holler, E., Rupley, J. A. and Hess, G. P. Productive and Unproductive Lysozyme-Chitosaccharide Complexes. Equilibrium Measurements. Biochemistry 14, 1088-(1975a).

Holler, E., Rupley, J. A. and Hess, G. P. Productive and Unproductive Lysozyme-Chitosaccharide Complexes. Kinetic Investigations. Biochemistry 14, 2377-(1975b).

Hurwitz, E. Wilchek, M. and Phita, J. Soluble Macromolecules as Carriers for Daunomycin. J. Appl. Biochem. 2, 25–35 (1980).

Hurwitz, E., Arnon, R., Sahar, E. and Danon, Y. A Conjugate of Adriamycin and Monoclonal Antibodies to Thy-1 Antigen Inhibits Human Neuroblastoma Cells In Vitro. Ann. N.Y. Acad. Sci. 417, 125–136 (1983).

Imoto, To, Johnson, L. N., North, A.C.T., Phillips, D.C. and Rupley, J. A. Vertebrate Lysozymes. In: The Enzymes (P. D. Boyer, ed.) Vol. 7, 665–868 (1972).

McCallister, T. J., Halpern, S. E., Dillman, R. O. and Shawler, D. L. Human Anti-Mouse Antibody (HAMA) Formation in Cancer Patients Following Single Injections of Murine Monoclonal Antibodies. FASEB J. 2:690 (1988).

Mitra S. and Lawton, R. G. Reagents For the Cross-Linking of Proteins by Equilibrium Transfer Alkylation. J. Amer. Chem. Soc. 101, 3097–3110 (1979).

Napper, A. D., Benkovic, S. J., Tramontano, A. and Lerner, R. A. A Stereospecific Cyclization Catalyzed by an Antibody. Science 237, 1041–1043 (1987).

Osserman, E. F. and Lawlor, D. P. Serum and Urinary Lysozyme (Muramidase) in Monocytic and Monomyelocytic Leukemia. J. Exp. Med. 124, 921–951 (1966).

Phillips, H. J. In: Tissue Culture: Methods and Applications (P. F. Kruse, Jr. and M. K. Patterson, Jr., eds.) p. 406 (1973).

Prakash, C. and Vijay, I .K. A New Fluorescent Tag for Labeling of Saccharides. Analyt. Biochem. 128, 41–46 (1983).

Raftery, M. A., Rand-Meir, T., Dahlquist, F. W. Parsons, S. M., Borders Jr., C. L., Wolcott, R. G., Beranek, Jr., W. and Jao, L. Separation of Glucosaminoglycan Saccharide and Glycoside Mixtures by Gel Filtration. Analyt. Biochem. 30, 427–435 (1969).

Reynolds, J. C., Carrasquillo, J. A., Keenan, A. M., Lora, M. E., Sugarbaken, P., Abrams, P., Foon, K., Mulshine, J. L., Roth, J., Colcher, D., Schlom, J. and Larson, S. M. Human Anti-murine Antibodies Following Immunoscintigraphy on Therapy With Radiolabeled Monoclonal Antibodies. J. Nucl. Med., 27, 1022 (1986).

Rodwell, J. D. and McKearn, T. J. Antibody Conjugates for the Delivery of Compounds to Target Sites. U.S. Pat. No. 4,671,958 Jun. 9, 1987.

Rupley, J. A. The Hydrolysis of Chitin. Biochem. Biophys. Acta 83, 245–255 (1964).

Schroff, R. W., Foon, K. A., Bratty, S. M., Oldham, R. K., and Morgan, Jr. A. C., Human Anti-Murine Immunoglobulin Responses in Patients Receiving Monoclonal Antibody Therapy. Cancer Res. 45, 879–885 (1985).

Searle, F., Bier, C., Buckley, R. G. and 8 others. The Potential of Carboxypeptidase $G_2$-Antibody Conjugates as Anti-Tumour Agents. Br. J. Cancer 53, 377 (1986).

Sela, M. and Hurwitz, E. Conjugates of Antibodies with Cytotoxic Drugs. In: Immunoconjugates. Antibody Conjugates in Radioimaging and Therapy of Cancer (C. -W. Vogel, ed. ), 189–216, (1987).

Senter, P. D., Saulnier, M. G., Schreiber, G. J., Hirschberg, D. L., Brown, J. P., Hellstroem, I. and Hellstroem, K. E. Anti-Tumor Effects of Antibody Alkaline Phosphatase Conjugates in Combination With Etoposide Phosphate. Proc. Natl. Acad. Sci. U.S.A. 85, 4842–4846 (1988).

Shugar, D. Measurement of Lysozyme Activity and the Ultraviolet Inactivation of Lysozymeo Biochem. Biophys. Acta, 8, 302–309, 1949.

Steis, R., Carrasquillo, J. A. and 16 others. An Evaluation of the Toxicity, Immunogenecity, and Tumor Radioimmunodetecting Ability of Two Human Monoclonal Antibodies in Patients with Metastatic Colorectal Carcinoma. J. Clin. Oncology, 1990 (in press).

Thorpe, P. E. Wallace, P. M., Knowles, P. P., Relf, M. G., Brown, A. N. F., Watson, G. J., Knyba, R. E., Wawrzyczak, E. J. and Blakey, D.C. New Coupling Agents for the Synthesis of Immunotoxins Containing a Hindered Disulfide Bond with Improved Stability In Vivo. Cancer Res. 47, 5924–5931 (1987).

Vogel, C. -W ted.) Immunoconjugates. Antibody Conjugates in Radioimaging and Therapy of Cancer. Oxford University Press, N.Y. 1987.

Wawrzynczak. E. J. and Thorpe, P. E. Methods for Preparing Immunotoxins: Effect of the Linkage on Activity and Stability. In: Immunoconjugates Antibody Conjugates in Radioimaging and Therapy of Cancer. (C. -W. Vogel, ed.), 28–55 (1987).

Young, R. C. and Ozols, R. F. The Anthracycline Antineoplastic Drugs. N. Engl. J. Med. 305, 139–153 (1981).

Zara, J. J., Wood, R. C., McCabe, R. P., Pomato, N., Hanna Jr., M. G., Bredehorst, R. and Vogel, C. -W. Synthesis of a Novel Site-Specific Heterobifunctional Crosslinker: Use for the Preparation of Antibody Conjugates with Cobra Venom Factor. Fourth International Conference on Monoclonal Antibody Immunoconjugates for Cancer, San Diego, Calif., Mar. 30th to Apr. 1, 1989.

We claim:

1. In an improved method for in vivo activation of a prodrug at the location of target tissue in a patient comprising:

a. administering an activator-targeting moiety conjugate comprising an activator conjugated with a targeting moiety that has an affinity for the target tissue and the activator has an activity that converts a prodrug into an active drug, said activator being linked to the targeting moiety; and thereafter b. administering a prodrug that is converted to an active drug by the activator on the conjugate;

wherein the improvement comprises using an activatortargeting moiety conjugate and prodrug that are essentially non-immunogenic in the patient, wherein said activator is lysozyme, said targeting moiety is an antibody or fraqment thereof and said prodrug is an anthracycline.

2. The method of claim 1, wherein the patient is a human and wherein the targeting moiety is selected from the group consisting of a human monoclonal antibody, chimeric monoclonal antibody consisting of primarily human components with antigen specificity conferred by non-human components, a natural hormone derivative or an analog of a natural hormone, an antigen derived from man or closely related species, and a genetically engineered or a synthetic analog of a human derived antibody component.

3. The method of claim 1, wherein the lysozyme is coupled to the targeting moiety by coupling agents selected from the group consisting of homo-bifunctional crosslinking agents, heterobifunctional crosslinking agents, and protein modifying reagents.

4. The method of claim 1, wherein the improvement further comprises repeatedly administering the prodrug.

5. The method of claim 1, wherein the improvement further comprises repeatedly administering the activator-targeting moiety conjugate.

6. The method of claims 1, wherein the improvement further comprises allowing the activator-targeting moiety conjugate to bind to target tissue and allowing unbound conjugate to clear from the patient before administering the prodrug.

7. The method of claim 6, wherein the activator-targeting moiety conjugate is cleared by extracorporeal means.

8. An activator-targeting moiety conjugate comprising lysozyme as the activator, wherein the targeting moiety is an antibody selected from the group consisting of a human monoclonal antibody, a monoclonal antibody fragment and a chimeric monoclonal antibody, and whereby said activator-targeting moiety is non-immunogenic in humans.

9. A prodrug comprising an anthracycline carrying a cleavable molecule that prevents cellular uptake.

10. The prodrug of claim 9, comprising an anthracycline derivatized with a chitin oligomer spacer.

11. The prodrug of claim 10, wherein the anthracycline is doxorubicin.

12. The prodrug of claim 11, wherein the chitin oligomer spacer is attached through an amino group at a site selected from the group consisting of the C13 carbonyl site on the anthracycline and the sugar moiety on the anthracycline.

13. The prodrug of claim 10, wherein the chitin oligomer derivative contains $(GlcNAc)_n$, where n is 1 to 10, carrying negatively charged groups and a reactive group allowing covalent attachment to the anthracycline.

14. The prodrug of claim 13, wherein the negatively charged groups represent sulfonates, phosphates, carboxylates or phosphonates.

15. The prodrug of claim 13, wherein the number of negatively charged groups is from 1 to 10.

16. The prodrug of claim 13, wherein the reactive group is selected from disulfide, thioester, imide, halogen, amine, carboxyl, ester, thiol and alcohol groups.

17. The prodrug of claim 10, wherein the chitin oligomer spacer is bound covalently to the drug through an active group selected from disulfide, thioester, imide, halogen, amine, carboxyl, ester, thiol and alcohol groups.

* * * * *

UNITED STATES PATENT AND TRADEMARK OFFICE
CERTIFICATE OF CORRECTION

PATENT NO. : 5,433,955
DATED : July 18, 1995
INVENTOR(S) : BREDEHORST ET AL.

It is certified that error appears in the above-indentified patent and that said Letters Patent is hereby corrected as shown below:

Column 17, claim 1, line 4, delete "tortargeting" and replace with -- tor-targeting --.

Column 17, claim 1, line 7, delete "fraqment" and replace with -- fragment --.

Column 17, claim 2, line 4, after "body", insert -- a --.

Signed and Sealed this

Twenty-seventh Day of February, 1996

Attest:

BRUCE LEHMAN

*Attesting Officer*   *Commissioner of Patents and Trademarks*